(12) United States Patent
Shneider et al.

(10) Patent No.: US 11,098,098 B2
(45) Date of Patent: Aug. 24, 2021

(54) METHODS AND COMPOSITIONS RELATING TO P62/SQSTM1 FOR THE TREATMENT AND PREVENTION OF INFLAMMATION-ASSOCIATED DISEASES

(71) Applicant: CureLab Oncology, Inc., Dedham, MA (US)

(72) Inventors: Alexander Shneider, Dedham, MA (US); Franco Venanzi, Camerino (IT); Dimitrios Agas, Camerino (IT); Antonio Concetti, Falerone (IT); Maria Giovanna Sabbieti, Camerino (IT); Vladimir Gabai, Brighton, MA (US); Michael Sherman, Newton, MA (US); Victor Shifrin, Newton, MA (US)

(73) Assignee: CureLab Oncology, Inc., Dedham, MA (US)

( * ) Notice: Subject to any disclaimer, the term of this patent is extended or adjusted under 35 U.S.C. 154(b) by 0 days.

(21) Appl. No.: 16/167,171

(22) Filed: Oct. 22, 2018

(65) Prior Publication Data

US 2019/0153056 A1    May 23, 2019

Related U.S. Application Data

(63) Continuation of application No. 15/108,653, filed as application No. PCT/US2014/072484 on Dec. 29, 2014, now abandoned.

(60) Provisional application No. 61/921,504, filed on Dec. 29, 2013, provisional application No. 61/949,597, filed on Mar. 7, 2014.

(51) Int. Cl.
| | |
|---|---|
| *C07K 14/545* | (2006.01) |
| *A61K 45/06* | (2006.01) |
| *A61K 38/17* | (2006.01) |
| *C07K 14/47* | (2006.01) |
| *A61K 39/00* | (2006.01) |
| *A61P 25/28* | (2006.01) |
| *A61P 37/06* | (2006.01) |
| *A61P 29/00* | (2006.01) |
| *A61K 31/436* | (2006.01) |
| *A61K 31/519* | (2006.01) |
| *A61K 31/573* | (2006.01) |
| *C07K 14/52* | (2006.01) |
| *C07K 14/525* | (2006.01) |
| *C07K 14/54* | (2006.01) |
| *C07K 16/24* | (2006.01) |
| *C12N 15/62* | (2006.01) |

(52) U.S. Cl.
CPC .......... *C07K 14/545* (2013.01); *A61K 31/436* (2013.01); *A61K 31/519* (2013.01); *A61K 31/573* (2013.01); *A61K 38/1709* (2013.01); *A61K 39/0005* (2013.01); *A61K 39/0008* (2013.01); *A61K 45/06* (2013.01); *A61P 25/28* (2018.01); *A61P 29/00* (2018.01); *A61P 37/06* (2018.01); *C07K 14/47* (2013.01); *C07K 14/523* (2013.01); *C07K 14/525* (2013.01); *C07K 14/5412* (2013.01); *C07K 16/245* (2013.01); *C07K 16/248* (2013.01); *C12N 15/62* (2013.01); *A61K 2039/53* (2013.01); *A61K 2039/55566* (2013.01)

(58) Field of Classification Search
CPC .................................................. C07K 14/545
See application file for complete search history.

(56) References Cited

U.S. PATENT DOCUMENTS

| | | | |
|---|---|---|---|
| 5,962,224 | A | 10/1999 | Shin et al. |
| 5,977,311 | A | 11/1999 | Andabalan et al. |
| 6,291,645 | B1 | 9/2001 | Shin et al. |
| 7,435,872 | B2 | 10/2008 | Shin et al. |
| 7,479,368 | B2 | 1/2009 | Brown et al. |
| 7,491,501 | B2 | 2/2009 | Wooten |
| 7,608,412 | B2 | 10/2009 | Wooten et al. |

(Continued)

FOREIGN PATENT DOCUMENTS

| | | |
|---|---|---|
| CA | 2844283 A1 | 2/2013 |
| CN | 1322730 A | 11/2001 |

(Continued)

OTHER PUBLICATIONS

Fixed Risk Factors, IOF, https://www.iofbonehealth.org/fixed-risk-factors, Oct. 3, 2007, 4 pages.

(Continued)

*Primary Examiner* — Scott Long

(57) ABSTRACT

Provided herein are novel p62 compositions for the modulation of expression of a proinflammatory cytokines, osteogenic transcription factors, a bone resorptive factors and endogenous p62. Consequently, such p62 compositions are useful for prophylaxis and treatment of inflammatory diseases and related methods. In certain embodiments the inflammatory diseases are not cancer-related. In various embodiments, the inflammatory diseases include, but are not limited to osteoporosis, obesity, metabolic syndrome, type 2 diabetes, fat liver, inflammatory bowel disease, chronic pancreatitis, asthma, chronic obstructive pulmonary disease (COPD), rheumatoid arthritis (RA), osteoarthritis, multiple sclerosis (MS), psoriasis, congestive heart failure (CHF), atherosclerosis, neurodegenerative diseases (ALS, Parkinson, Alzheimer's, Huntington disease), depression, schizophrenia, gout, asbestosis and silicosis.

6 Claims, 12 Drawing Sheets

Specification includes a Sequence Listing.

(56) References Cited

U.S. PATENT DOCUMENTS

| | | | |
|---|---|---|---|
| 2002/0168360 A1* | 11/2002 | Dingivan | A61P 37/08 424/143.1 |
| 2003/0235558 A1 | 12/2003 | Shin et al. | |
| 2006/0035823 A1 | 2/2006 | Lederman et al. | |
| 2006/0263774 A1* | 11/2006 | Clark | A61P 31/20 435/6.14 |
| 2007/0238643 A1 | 10/2007 | Wooten et al. | |
| 2008/0132460 A1 | 6/2008 | Shin et al. | |
| 2009/0215895 A1 | 8/2009 | Ferrante et al. | |
| 2011/0287974 A1 | 11/2011 | Benvenisty et al. | |
| 2012/0295800 A1 | 11/2012 | Sharma | |
| 2017/0043002 A1 | 2/2017 | Shneider et al. | |

FOREIGN PATENT DOCUMENTS

| | | |
|---|---|---|
| CN | 103889440 A | 6/2014 |
| WO | 97/22255 A1 | 6/1997 |
| WO | 2003012134 | 2/2003 |
| WO | 2003012134 A2 | 2/2003 |
| WO | 2005050170 A2 | 6/2005 |
| WO | 2007044522 A1 | 4/2007 |
| WO | 2011039734 A2 | 4/2011 |
| WO | 2013022991 | 2/2013 |
| WO | 2013022991 A2 | 2/2013 |
| WO | 2015050353 | 4/2015 |
| WO | 2015050383 A1 | 4/2015 |
| WO | 2015/100446 A1 | 7/2015 |

OTHER PUBLICATIONS

International Preliminary Report on Patentability received for PCT International Application No. PCT/US14/72484, dated Jul. 14, 2016, 10 pages.

SQSTM1, The Human Protein Atlas, retrieved from web: <https://www.proteinatlas.org/ENSG00000161011-SQSTM1/tissue#gene_information> on Apr. 19, 2018, 4 pages.

Database Genbank (Apr. 8, 2018) "*Homo sapiens* sequestosome 1 (SQSTM1), transcript variant 1, mRNA", Genbank Accession No. NM_003900.4, 9 pages.

Rost (1999) "Twilight zone of protein sequence alignments", Protein Engineering, 12(2):85-94.

Stein (2009) "Afterbirth: It's What's for Dinner", Time, 174(1):2 pages.

Geetha et al., "Sequestome 1/p62:across diseases", Biomarkers, 2012, 17:99-103.

Park et al., "p62/SQSTM1 Enhances NOD2-Mediated Signaling and Cytokine Production through Stabilizing NOD2 Oligomerization", PLOS One, 2013, 8(2):e57138;1-11.

Sabbieti et al., "Plasmid DNA-coding p62 as a bone effective anti-inflammatory / anabolic agent", Oncotarget, 2015, 6:3590-3599.

Extended European Search Report dated Jul. 7, 2017 in European Application No. EP14874099.6 filed Jul. 27, 2016, based on International Application No. PCT/US2014/072484 filed Dec. 29, 2014 and published as:WO 015/100446 on: Jul. 2, 2015.

Korb et al., "The TRAF6 Binding Molecule p62/SQSTM1 is a Critical Regulator of Inflammatory Bone Destruction", Ann Rheum Dis 69, No Suppl 2, A19.

Manley et al.., "The Role of p62/Sqstmi in Liver Physiology and Pathogenesis", Exp Biol Med 238, 2013, 525-538.

Raison et al., "Is Depression an Inflammatory Disorder?", Cuff Psychiatry Rep 13, 2011, 467-475.

Salminen et al., "Emerging Role of p62/sequestome-1 in the Pathogenesis of Alzheimer's Disease", Prog. Neurobiol 96, 2012, 87-95.

International Search Report and Written Opinion dated Apr. 16, 2015 in International Application No. PCT/US14/072484, published as WO 2015/100446 on Jul. 2, 2015.

Korb, et al. "The TRAF6 Binding Molecule p62/SQSTM1 is a critical Regulator of Inflammatory Bone Destruction." Ann Rheum Dis 2010 69: A19.

Manley, et al. "Role of p62/SASTM1 in liver physiology and pathogenesis." Experimental Biology and Medicine 2013; 238: 525-538.

Salminen, et al. "Emerging role of p62/sequestosome-1 in the pathogenesis of Alzheimer's disease." Progress in Neurobiology 96 (2012) 87-95.

Raison, et al. "Is Depression an Inflammatory Disorder?" Curr Psychiatry Rep. Dec. 2011; 13(6): 467-475.

\* cited by examiner

```
   1 cctctcgagg cggggcgggg cctccgcgtt cgctacaaaa gccgcgcggc ggctgcgacc
  61 gggacggccc gttttccgcc agctcgccgc tcgctatggc gtcgctcacc gtgaaggcct
 121 accttctggg caaggaggac gcggcgcgcg agattcgccg cttcagcttc tgctgcagcc
 181 ccgagcctga ggcggaagcc gaggctgcgg cgggtccggg acctgcgag cggctgctga
 241 gccgggtggc cgccctgttc ccgcgctgc ggcctggcgg cttccaggcg cactaccgcg
 301 atgaggacgg ggacttggtt gccttttcca gtgacgagga attgacaatg ccatgtcct
 361 acgtgaagga tgacatcttc cgaatctaca ttaaagagaa aaaagagtgc cggcgggacc
 421 accgcccacc gtgtgctcag gaggcgcccc gcaacatggt gcacccaat gtgatctgcg
 481 atggctgcaa tgggcctgtg gtaggaaccc gctacaagtg cagcgtctgc cagactacg
 541 acttgtgtag cgtctgcgag ggaaagggct gcaccgggg gcacaccaag ctcgcattcc
 601 ccagcccctt cgggcacctg tctgaggct ctcgcacag ccgctggctc cggaaggtga
 661 aacacggaca cttcgggtgg ccaggatggg aaatgggtcc accaggaaac tggagcccac
 721 gtcctcctcg tgcaggggag gcccgccctg gccccacggc agaatcagct tctggtccat
 781 cggaggatcc gagtgtgaat tcctgaaga acgttgggga gagtgtggca gctgcccta
 841 gccctctggg cattgaagtt gatatcgatg tggagcacgg agggaaaaga agccgcctga
 901 ccccgtctc tccagagagt tccagcacag aggagaagag cagctcacag ccaagcagct
 961 gctgctctga ccccagcaag ccgggtggga atgttgaggg cgccacgcag tctctggcgg
1021 agcagatgag gaagatcgcc ttggagtccg aggggcgccc tgaggaacag atggagtcgg
1081 ataactgttc aggaggagat gatgactgga cccatctgtc ttcaaaagaa gtggacccgt
1141 ctacaggtga actccagtcc ctacagatgc cagaatccga agggccaagc tctctggacc
1201 cctcccagga gggacccaca gggctgaagg aagctgcctt gtacccacat ctcccgccag
1261 aggctgaccc gcggctgatt gagtccctct cccagatgct gtccatgggc ttctctgatg
1321 aaggcggctg gctcaccagg ctcctgcaga ccaagaacta tgacatcgga gcggctctgg
1381 acaccatcca gtattcaaag catccccgc cgttgtgacc acttttgccc acctcttctg
1441 cgtgccctc ttctgtctca tagttgtgtt aagcttgcgt agaattgcag gtctctgtac
1501 gggccagttt ctctgccttc ttccaggatc aggggttagg gtgcaagaag ccatttaggg
1561 cagcaaaaca agtgacatga agggagggtc cctgtgtgtg tgtgctga tgtttcctgg
1621 gtgccctggc tccttgcagc agggctgggc ctgcgagacc caaggctcac tgcagcgcgc
1681 tcctgacccc tccctgcagg ggctacgtta gcagccagc acatagcttg cctaatggct
1741 ttcactttct cttttgtttt aaatgactca taggtccctg acatttagtt gattattttc
1801 tgctacagac ctggtacact ctgattttag ataaagtaag cctaggtgtt gtcagcaggc
1861 aggctgggga ggccagtgtt gtgggcttcc tgctgggact gagaaggctc acgaagggca
1921 tccgcaatgt tggtttcact gagagctgcc tcctggtctc ttcaccactg tagttctctc
1981 atttccaaac catcagctgc ttttaaaata agatctcttt gtagccatcc tgttaaattt
2041 gtaaacaatc taattaaatg gcatcagcac tttaaccaat gacgtttgca tagagagaaa
2101 tgattgacag taagtttatt gttaatggtt cttacagagt atctttaaaa gtgccttagg
2161 ggaaccctgt ccctcctaac aagtgtatct cgattaataa cctgccagtc ccagatcaca
2221 catcatcatc gaagtcttcc ccagttataa agaggtcaca tagtcgtgtg ggtcgaggat
2281 tctgtgcctc caggaccagg ggcccaccct ctgcccaggg agtccttgcg tccatgaggg
2341 tcttcccgca aggcctctca gacccagatg tgacggggtg tgtggcccga ggaagctgga
2401 cagcggcagt gggcctgctg aggccttctc ttgaggcctg tgctctgggg tcccttgct
2461 tagcctgtgc tggaccagct ggcctgggt ccctctgaag agacttggc tgctcactgt
2521 ccacatgtga acttttctta ggtggcagga caaattgcgc ccatttagag gatgtggctg
2581 taacctgctg gatgggactc catagctcct tccaggacc cctcagctcc ccggcactgc
2641 agtctgcaga gttctcctgg aggcagggc tgctgccttg tttcaccttc catgtcaggc
2701 cagcctgtcc ctgaaagaga agatggccat gccctccatg tgtaagaaca atgccagggc
2761 ccaggaggac cgcctgccct gcctgggcct tggctgggcc tctggttctg acactttctg
2821 ctggaagctg tcaggctggg acaggctttg attttgaggg ttagcaagac aaagcaaata
2881 aatgccttcc acctcaccgc aaaaaaaaaa aaaaaaaaaa aaa
    (SEQ ID NO: 1)
```

FIG. 1

MASLTVKAYLLGKEDAAREIRRFSFCCSPEPEAEAEAAAGPGPC
ERLLSRVAALFPALRPGGFQAHYRDEDGDLVAFSSDEELTMAMSYVKDDIFRIYIKEK
KECRRDHRPPCAQEAPRNMVHPNVICDGCNGPVVGTRYKCSVCPDYDLCSVCEGKGLH
RGHTKLAFPSPFGHLSEGFSHSRWLRKVKHGHFGWPGWEMGPPGNWSPRPPRAGEARP
GPTAESASGPSEDPSVNFLKNVGESVAAALSPLGIEVDIDVEHGGKRSRLTPVSPESS
STEEKSSSQPSSCCSDPSKPGGNVEGATQSLAEQMRKIALESEGRPEEQMESDNCSGG
DDDWTHLSSKEVDPSTGELQSLQMPESEGPSSLDPSQEGPTGLKEAALYPHLPPEADP
RLIESLSQMLSMGFSDEGGWLTRLLQTKNYDIGAALDTIQYSKHPPPL (SEQ ID NO: 2)

FIG. 2

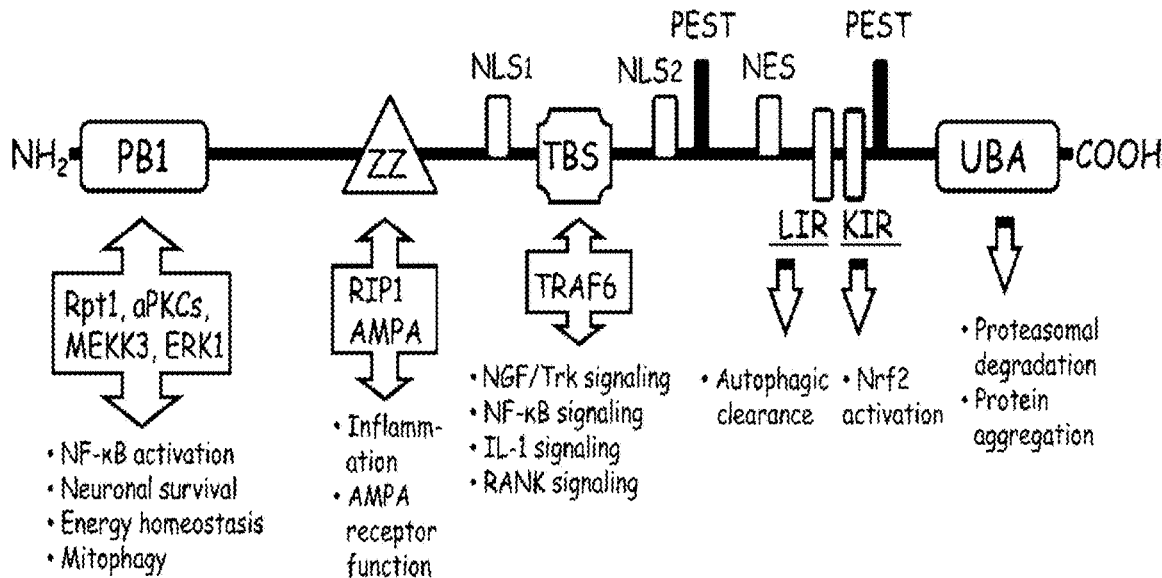

FIG. 3

SEQUENCE LISTING

```
<160> NUMBER OF SEQ ID NOS: 2

<210> SEQ ID NO 1
<211> LENGTH: 2923
<212> TYPE: DNA
<213> ORGANISM: Homo sapiens

<400> SEQUENCE: 1
cctctcgagg cggggcgggg cctccgcgtt cgctacaaaa gccgcgcggc ggctgcgacc      60
gggacggccc gttttccgcc agctcgccgc tcgctatggc gtcgctcacc gtgaaggcct     120
accttctggg caaggaggac gcggcgcgcg agattcgccg cttcagcttc tgctgcagcc     180
ccgagcctga ggcggaagcc gaggctgcgg cgggtccggg accctgcgag cggctgctga     240
gccgggtggc cgccctgttc cccgcgctgc ggcctggcgg cttccaggcg cactaccgcg     300
atgaggacgg ggacttggtt gccttttcca gtgacgagga attgacaatg gccatgtcct     360
acgtgaagga tgacatcttc cgaatctaca ttaaagagaa aaaagagtgc cggcgggacc     420
accgcccacc gtgtgctcag gaggcgcccc gcaacatggt gcaccccaat gtgatctgcg     480
atggctgcaa tgggcctgtg gtaggaaccc gctacaagtg cagcgtctgc ccagactacg     540
acttgtgtag cgtctgcgag ggaaagggct tgcaccgggg gcacaccaag ctcgcattcc     600
ccagcccctt cggggcacctg tctgagggct tctcgcacag ccgctggctc cggaaggtga     660
aacacggaca cttcgggtgg ccaggatggg aaatgggtcc accaggaaac tggagcccac     720
gtcctcctcg tgcaggggag gcccgccctg gccccacggc agaatcagct tctggtccat     780
cggaggatcc gagtgtgaat ttcctgaaga acgttgggga gagtgtggca gctgccctta     840
gccctctggg cattgaagtt gatatcgatg tggagcacgg agggaaaaga agccgcctga     900 ccccgtctc tccagagagt tccagcacag aggagaagag cagctcacag ccaagcagct     960
gctgctctga ccccagcaag ccgggtggga atgttgaggg cgccacgcag tctctggcgg    1020
agcagatgag gaagatcgcc ttggagtccg aggggcgccc tgaggaacag atggagtcgg    1080
ataactgttc aggaggagat gatgactgga cccatctgtc ttcaaaagaa gtggacccgt    1140
ctacaggtga actccagtcc ctacagatgc cagaatccga agggccaagc tctctggacc    1200
cctcccagga gggacccaca gggctgaagg aagctgcctt gtacccacat ctcccgccag    1260
aggctgaccc gcggctgatt gagtccctct cccagatgct gtccatgggc ttctctgatg    1320
aaggcggctg gctcaccagg ctcctgcaga ccaagaacta tgacatcgga gcggctctgg    1380
```

-continued

```
acaccatcca gtattcaaag catccccgc cgttgtgacc acttttgccc acctcttctg    1440
cgtgcccctc ttctgtctca tagttgtgtt aagcttgcgt agaattgcag gtctctgtac    1500
gggccagttt ctctgccttc ttccaggatc aggggttagg gtgcaagaag ccatttaggg    1560
cagcaaaaca agtgacatga agggagggtc cctgtgtgtg tgtgtgctga tgtttcctgg    1620
gtgccctggc tccttgcagc agggctgggc ctgcgagacc caaggctcac tgcagcgcgc    1680
tcctgacccc tccctgcagg ggctacgtta gcagcccagc acatagcttg cctaatggct    1740
ttcactttct cttttgtttt aaatgactca taggtccctg acatttagtt gattattttc    1800
tgctacagac ctggtacact ctgattttag ataaagtaag cctaggtgtt gtcagcaggc    1860
aggctgggga ggccagtgtt gtgggcttcc tgctgggact gagaaggctc acgaagggca    1920
tccgcaatgt tggtttcact gagagctgcc tcctggtctc ttcaccactg tagttctctc    1980
atttccaaac catcagctgc ttttaaaata agatctcttt gtagccatcc tgttaaattt    2040
gtaaacaatc taattaaatg gcatcagcac tttaaccaat gacgtttgca tagagagaaa    2100
tgattgacag taagtttatt gttaatggtt cttacagagt atctttaaaa gtgccttagg    2160
ggaaccctgt ccctcctaac aagtgtatct cgattaataa cctgccagtc ccagatcaca    2220
catcatcatc gaagtcttcc ccagttataa agaggtcaca tagtcgtgtg ggtcgaggat    2280
tctgtgcctc caggaccagg ggcccaccct ctgcccaggg agtccttgcg tcccatgagg    2340
tcttcccgca aggcctctca gacccagatg tgacggggtg tgtggcccga ggaagctgga    2400
cagcggcagt gggcctgctg aggccttctc ttgaggcctg tgctctgggg gtcccttgct    2460
tagcctgtgc tggaccagct ggcctggggt ccctctgaag agaccttggc tgctcactgt    2520
ccacatgtga acttttttcta ggtggcagga caaattgcgc ccatttagag gatgtggctg    2580
taacctgctg gatgggactc catagctcct tcccaggacc cctcagctcc ccggcactgc    2640
agtctgcaga gttctcctgg aggcaggggc tgctgccttg tttcaccttc catgtcaggc    2700
cagcctgtcc ctgaaagaga agatggccat gccctccatg tgtaagaaca atgccagggc    2760
ccaggaggac cgcctgccct gcctgggcct tggctgggcc tctggttctg acactttctg    2820
ctggaagctg tcaggctggg acaggctttg attttgaggg ttagcaagac aaagcaaata    2880
aatgccttcc acctcaccgc aaaaaaaaaa aaaaaaaaa aaa                      2923
```

<210> SEQ ID NO 2
<211> LENGTH: 440
<212> TYPE: PRT
<213> ORGANISM: Homo sapiens

<400> SEQUENCE: 2

```
Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95
```

```
Ile Tyr Ile Lys Glu Lys Lys Glu Cys Arg Arg Asp His Arg Pro Pro
            100                 105                 110
Cys Ala Gln Glu Ala Pro Arg Asn Met Val His Pro Asn Val Ile Cys
            115                 120                 125
Asp Gly Cys Asn Gly Pro Val Val Gly Thr Arg Tyr Lys Cys Ser Val
            130                 135                 140
Cys Pro Asp Tyr Asp Leu Cys Ser Val Cys Glu Gly Lys Gly Leu His
145                 150                 155                 160
Arg Gly His Thr Lys Leu Ala Phe Pro Ser Pro Phe Gly His Leu Ser
                165                 170                 175
Glu Gly Phe Ser His Ser Arg Trp Leu Arg Lys Val Lys His Gly His
            180                 185                 190
Phe Gly Trp Pro Gly Trp Glu Met Gly Pro Pro Gly Asn Trp Ser Pro
            195                 200                 205
Arg Pro Pro Arg Ala Gly Glu Ala Arg Pro Gly Pro Thr Ala Glu Ser
210                 215                 220
Ala Ser Gly Pro Ser Glu Asp Pro Ser Val Asn Phe Leu Lys Asn Val
225                 230                 235                 240
Gly Glu Ser Val Ala Ala Ala Leu Ser Pro Leu Gly Ile Glu Val Asp
                245                 250                 255
Ile Asp Val Glu His Gly Gly Lys Arg Ser Arg Leu Thr Pro Val Ser
            260                 265                 270
Pro Glu Ser Ser Ser Thr Glu Glu Lys Ser Ser Ser Gln Pro Ser Ser
            275                 280                 285
Cys Cys Ser Asp Pro Ser Lys Pro Gly Gly Asn Val Glu Gly Ala Thr
290                 295                 300
Gln Ser Leu Ala Glu Gln Met Arg Lys Ile Ala Leu Glu Ser Glu Gly
305                 310                 315                 320
Arg Pro Glu Glu Gln Met Glu Ser Asp Asn Cys Ser Gly Gly Asp Asp
                325                 330                 335
Asp Trp Thr His Leu Ser Ser Lys Glu Val Asp Pro Ser Thr Gly Glu
            340                 345                 350
Leu Gln Ser Leu Gln Met Pro Glu Ser Glu Gly Pro Ser Ser Leu Asp
            355                 360                 365
Pro Ser Gln Glu Gly Pro Thr Gly Leu Lys Glu Ala Ala Leu Tyr Pro
370                 375                 380
His Leu Pro Pro Glu Ala Asp Pro Arg Leu Ile Glu Ser Leu Ser Gln
385                 390                 395                 400
Met Leu Ser Met Gly Phe Ser Asp Glu Gly Gly Trp Leu Thr Arg Leu
                405                 410                 415
Leu Gln Thr Lys Asn Tyr Asp Ile Gly Ala Ala Leu Asp Thr Ile Gln
            420                 425                 430
Tyr Ser Lys His Pro Pro Leu
            435                 440
```

METHODS AND COMPOSITIONS RELATING TO P62/SQSTM1 FOR THE TREATMENT AND PREVENTION OF INFLAMMATION-ASSOCIATED DISEASES

CROSS REFERENCE TO RELATED APPLICATIONS

This application is a continuation of U.S. patent application Ser. No. 15/108,653 filed on Jun. 28, 2016, entitled "Methods and Compositions Relating to p62/SQSTM1 for the Treatment and Prevention of Inflammation-Associated Disease", naming Alexander Shneider, Franco Venanzi, Dimitrios Agas, Antonio Concetti, Maria Giovanna Sabbieti, Vladimir Gabai, Michael Sherman, and Victor Shifrin as inventors, which is a national stage application of international patent application no. PCT/US14/72484, filed on Dec. 29, 2014, entitled "Methods and Compositions Relating to p62/SQSTM1 for the Treatment and Prevention of Inflammation-Associated Disease", naming Alexander Shneider, Franco Venanzi, Dimitrios Agas, Antonio Concetti, Maria Giovanna Sabbieti, Vladimir Gabai, Michael Sherman, and Victor Shifrin as inventors, which claims the benefit of priority to U.S. Provisional Patent Application Ser. No. 61/921,504, filed Dec. 29, 2013 and entitled "Method of Use of Vectors, Encoding Products of the SQSTM1 Gene as Therapeutic and Preventive Agents for Osteoporosis", naming Alexander Shneider, Franco Venanzi, Dimitrios Agas, Antonio Concetti, Maria Giovanna Sabbieti, Vladimir Gabai, Michael Sherman, and Victor Shifrin as inventors, and to U.S. Provisional Patent Application Ser. No. 61/949,597, filed Mar. 7, 2014 and entitled "Methods and Compositions Relating to p62 for the Treatment and Prevention of Inflammation-Associated Disease", naming Alexander Shneider, Franco Venanzi, Dimitrios Agas, Antonio Concetti, Maria Giovanna Sabbieti, Vladimir Gabai, Michael Sherman, and Victor Shifrin as inventors. The entire content of all aforementioned applications are incorporated herein by reference, including all text, tables and drawings.

FIELD OF THE INVENTION

This invention relates generally to prevention and treatment of inflammatory diseases. More specifically, the invention relates to prevention and treatment of inflammatory diseases by administration of p62 compositions.

BACKGROUND OF THE INVENTION

Inflammation is an essential immune response that enables survival during infection or injury and maintains tissue homeostasis under a variety of noxious conditions. It can be divided in acute and chronic inflammation. Acute inflammation is a protective response to pathogens like bacteria and viruses, or to tissue damage. In response to infection or tissue damage, macrophages induce production of inflammatory cytokines (e.g., TNF, IL-1, IL-6) and chemokines (e.g., CCL2 and CXCL8), as well as prostaglandins.

These inflammatory mediators then act on target tissues, including local blood vessels, to induce vasodilation, extravasation of neutrophils, and leakage of plasma into the infected tissue. In addition, IL-1, TNF, and IL-6 can have systemic effects when secreted in sufficient amounts. They induce liver cells (hepatocytes) to produce acute phase proteins such as C-reactive protein and coagulation factors, and they activate brain endothelium to produce prostaglandins, including the major proinflammatory prostaglandin, PGE2. Locally produced PGE2, in turn, induces specific populations of neurons in the central nervous system to promote so-called sickness behavior: fever, anorexia, fatigue, sleepiness, and social withdrawal (Pecchi et al. 2009. Prostaglandins and sickness behavior: old story, new insights. Physiol Behav 97:279-292). In the case of sterile tissue injury in the absence of infection, acute inflammation promotes tissue repair and helps to prevent colonization of the damaged tissues by opportunistic pathogens. The usual result of acute inflammation is protection from the spread of infection, followed by resolution—the restoration of affected tissues to their normal structural and functional state. The major transcription factors involved in inflammation are NF-kappa-B and Stat-3.

If the inflammatory trigger is not eliminated by the acute inflammatory response or persists for any other reason, the resolution phase may not be appropriately induced and a chronic inflammatory state may ensue. This state can be caused by chronic infections, unrepaired tissue damage, persistent allergens, undigestable foreign particles, or endogenous crystals, such as monosodium urate (Majno 2004. Cell, Tissues, and Disease; Kumar 2003. Robbins Basic Pathology.) The chronic inflammatory response in these cases is typically localized to the site where the inflammatory inducer is present and often results in different types of local tissue remodeling.

In addition, a growing number of chronic inflammatory conditions have been described where the initiating trigger is not well defined but does not seem to involve infection or tissue damage. These inflammatory conditions are of particular interest because they accompany many diseases of industrialized countries, including obesity and type 2 diabetes, atherosclerosis, neurodegenerative diseases, and cancer. In these cases of chronic inflammation there appear to be vicious cycles connecting inflammation and the pathological process it accompanies.

Thus, obesity can lead to inflammation, whereas chronic inflammation can promote obesity-associated diabetes in part by inducing insulin resistance (Hotamisligil 2006. Inflammation and metabolic disorders. Nature 444:860-867). Similar positive feedback loops are present in atherosclerosis, cancer, and other chronic inflammatory diseases. An excessive inflammatory response is detrimental due to its negative effect on tissue function and, when extreme, results in overt tissue damage. Frequently, acute and chronic inflammation coexist over long periods, implying continual reinitiation. Examples are found in rheumatoid arthritis, asthma, chronic obstructive pulmonary disease (COPD), multiple sclerosis, Crohn's disease, ulcerative colitis, and cancers whose stroma is infiltrated both by macrophages and immature myeloid cells (Mantovani et al. 2008. Cancer-related inflammation. Nature 454:436-444) No single phenomenon contributes more to the medical burden in industrialized societies than chronic inflammation. Chronic inflammation contributes significantly to pathogenesis of atherosclerosis, obesity, cancer, chronic obstructive pulmonary disease, asthma, inflammatory bowel disease, neurodegenerative disease, multiple sclerosis, or rheumatoid arthritis and other diseases.

Osteoporosis is the most common disease of the bone associated with bone loss and affecting mostly women after onset of menopause. Menopause leads to decrease in estrogen levels, thus ovariectomy in rodents leading to cessation of estrogen generation is the most common model for osteoporosis. Postmenopausal period is marked by elevation of cytokines such us IL-6, TNF-alpha and IL-1beta, and the same cytokines are elevated under ovariectomy. TNF and IL-1 have potent antiapoptotic effects in OCs, prolonging OC lifespan, accelerating bone resorption and inhibiting bone formation, and blockade of TNF-alpha and IL-1beta prevents osteoporosis due to estrogen deficiency (Mundy 2007. Osteoporosis and Inflammation. Nutrition Reviews 65:S147-S151; Lencel and Magne 2011. Inflammaging: The driving force in osteoporosis? Medical Hypotheses 76:317-321).

Amyotrophic lateral sclerosis (ALS), or Lou Gehrig's disease, is a progressive fatal neurodegenerative disease that affects motor neurons in the brainstem, spinal cord, and motor cortex. ALS is universally fatal, with a median age of onset of 55 years and a survival of 2-5 years after the onset of symptoms. Prominent neuroinflammation can be easily observed in pathologically affected areas of the CNS and in spinal cords from both human ALS patients and mouse models of the disease (Smith et al. 2012. Role of pro-inflammatory cytokines released from microglia in neuro-degenerative diseases. Brain Res Bull 87:10-20). Typically, inflammation in ALS is characterized by gliosis and the accumulation of large numbers of activated microglia and astrocytes. Activation of glia in ALS has been extensively characterized and is marked by elevated production of potentially cytotoxic molecules such as ROS, inflammatory mediators such as COX-2, and proinflammatory cytokines such as IL-1beta, TNF-alpha, and IL-6 (Smith et al. 2012. Role of pro-inflammatory cytokines released from microglia in neurodegenerative diseases. Brain Res Bull 87:10-20). The most common mouse model of ALS is transgenic mouse expressing mutant form of superoxide dismutase, the same mutant form as seen in some ALS patients.

Multiple Sclerosis

Multiple sclerosis (MS) is a heterogeneous and complex autoimmune disease that is characterized by inflammation, demyelination, and axon degeneration in the CNS. This pathology results from a primary defect in the immune system that targets components of the myelin sheath, resulting in secondary effects on neurons. MS is considered an immune-mediated disease characterized by the presence of inflammatory demyelinating lesions in the CNS. Infection by bacteria or viruses or other environmental stimuli trigger the activation of microglia and astrocytes in multiple sclerosis (MS), leading to the production of proinflammatory cytokines through activation of the transcription factors NF-kappa-B and AP-1 (Luessi et al. 2012. Neurodegeneration in multiple sclerosis: novel treatment strategies. Expert Rev Neurother 12:1061-1076). Experimental autoimmune encephalomyelitis (EAE), in which rodents are immunized with a myelin-derived antigen and adjuvant, is the most common animal model of MS. By varying the genetic background and immunization protocol, EAE can reproduce the symptoms of the major forms of human MS.

There are two major classes of anti-inflammatory drugs, chemicals and biologicals. The first class includes such well-known drugs as aspirin, glucocorticoids, non-steroidal anti-inflammatory agents (celecoxib) and other agents (e.g., methotrexate, cyclosporine, rapamycin etc.). The second class includes agents that reduce activity of specific cytokines or their receptors, e.g., antibodies to TNF (see scheme below). Despite a variety of drugs, there is no treatment to cure chronic inflammation. In many instances existing drugs are not quite effective, very expensive and have numerous side effects. For instance, major drawbacks of anti-cytokine therapy is a decreased host immune defense against infection and expense.

p62 is a multifunctional protein that binds ubiquitin and regulates autophagy, activity of the nuclear factor kappa-B and some other signaling pathways. The protein functions as a scaffolding/adaptor protein in concert with TNF receptor-associated factor 6 (TRF6) to mediate activation of NF-kappa-B in response to upstream signals. Alternatively spliced transcript variants encoding either the same or different isoforms have been identified for this gene.

p62 was identified as 62-kDa protein that binds the src homology 2 (SH2) domain of tyrosine kinase Lckp56 in a phosphotyrosine-independent manner (Moscat et al. 2007. Signal integration and diversification through the p62 scaffold protein. Trends Biochem Sci 32:95-100). The primary sequence of p62 is known, and p62 was shown to bind ubiquitin. (Moscat et al. 2007. Signal integration and diversification through the p62 scaffold protein. Trends Biochem Sci 32:95-100). FIG. 1 shows the nucleic acid sequence of the cDNA and FIG. 2 the amino acid sequence.

SUMMARY OF THE INVENTION

Provided herein are methods to modulate the expression of a proinflammatory cytokine in a subject by administering to the subject an agent that includes: (a) at least 30 amino acids of a p62/SQSTM1 polypeptide or a variant thereof; or, (b) a p62/SQSTM1 encoding nucleic acid, wherein said p62/SQSTM1 encoding nucleic acid encodes at least 30 amino acids of a p62/SQSTM1 polypeptide or a variant thereof. The proinflammatory cytokine can be TNFα, IL-6, IL-1b, RANTES, IL-17, IL-23, CCL-1, MCP-5, or CXCL2.

Also provided herein are methods to modulate the expression of an osteogenic transcription factor in a subject by administering to the subject an agent that includes: (a) at least 30 amino acids of a p62/SQSTM1 polypeptide or a variant thereof; or, (b) a p62/SQSTM1 encoding nucleic acid, wherein said p62/SQSTM1 encoding nucleic acid encodes at least 30 amino acids of a p62/SQSTM1 polypeptide or a variant thereof. The osteogenic transcription factor can be osterix or runx2.

Also provided herein are methods to modulate the expression of a bone resorptive factor in a subject by administering to the subject an agent that includes: (a) at least 30 amino acids of a p62/SQSTM1 polypeptide or a variant thereof; or, (b) a p62/SQSTM1 encoding nucleic acid, wherein said p62/SQSTM1 encoding nucleic acid encodes at least 30 amino acids of a p62/SQSTM1 polypeptide or a variant thereof. The bone resorptive factor can be TNFα or RANKL.

Also provided herein are methods to modulate the expression of endogenous p62/SQSTM1 in a subject by administering to the subject an agent comprising that includes: (a) at least 30 amino acids of a p62/SQSTM1 polypeptide or a variant thereof; or, (b) a p62/SQSTM1 encoding nucleic acid, wherein said p62/SQSTM1 encoding nucleic acid encodes at least 30 amino acids of a p62/SQSTM1 polypeptide or a variant thereof.

Provided herein are methods to treat, alleviate, ameliorate, relieve, delay onset of, inhibit progression of, reduce severity of, or reduce incidence of one or more symptoms of a non-cancer-related chronic inflammatory disease in a subject by administering to the subject an agent comprising that includes: (a) at least 30 amino acids of a p62/SQSTM1 polypeptide or a variant thereof; or, (b) a p62/SQSTM1 encoding nucleic acid, wherein said p62/SQSTM1 encoding nucleic acid encodes at least 30 amino acids of a p62/SQSTM1 polypeptide or a variant thereof.

Any of the above methods can include administration of a variant p62/SQSTM1, wherein the variant is at least 80%, at least 85%, at least 90%, at least 91%, at least 92%, at least 93%, at least 94%, at least 95%, at least 96%, at least 97%, at least 98%, or at least 99% homologous to any sequence selected from the group consisting of SEQ. ID. NO. 2-35 10. The variant can have at least 80%, at least 85%, at least 90%, at least 91%, at least 92%, at least 93%, at least 94%, at least 95%, at least 96%, at least 97%, at least 98%, or at least 99% sequence homology to any sequence selected from the group consisting of SEQ. ID. NO. 2-35, or identical thereto.

Any of the above methods can include administration of p62-encoding nucleic acid comprises the sequence of SEQ ID NO:1.

Any of the above methods can include administration of p62 polypeptide or variant thereof having at least one domain deletion. The deleted domain can be PB1, ZZ, NLS2, TB, NLS1, NES, LIR, KIR, and UBA.

Any of the above methods can include administration of an agent including a p62 encoding nucleic acid, wherein said p62 encoding nucleic acid encodes a polypeptide, which is at least 95% identical to SEQ ID NO. 2, and wherein said p62 encoding nucleic acid further comprises a plasmid, RNA or a viral vector.

Any of the above methods can include p62/SQSTM1 polypeptide or p62/SQSTM1 encoding nucleic acid further including a fusion polypeptide or nucleic acid encoding for a fusion polypeptide, respectively.

Any of the above methods can include p62/SQSTM1 polypeptide or p62/SQSTM1 encoding nucleic acid in the form of a vaccine and further include administering an adjuvant to said subject. The adjuvant can be gel-type, microbial, particulate, oil-emulsion, surfactant-based, and synthetic adjuvant.

The non-cancer-related chronic inflammatory disease can be obesity, metabolic syndrome, type 2 diabetes, fat liver, Crohn's Disease, pancreatitis, asthma, chronic obstructive pulmonary disease, arthritis, osteoporosis, osteoarthritis, multiple sclerosis, psoriasis, congestive heart failure atherosclerosis, neurodegenerative diseases, gout, asbestosis, and silicosis. The neurodegenerative disease can be amyotrophic lateral sclerosis, Parkinson's disease, Huntington's disease, or Alzheimer's disease.

The methods to treat, alleviate, ameliorate, relieve, delay onset of, inhibit progression of, reduce severity of, or reduce incidence of one or more symptoms of a non-cancer-related chronic inflammatory disease in a subject can further include administering an anti-inflammatory therapy to said subject.

Any of the above methods can be applied to a subject that is a subject diagnosed with an inflammatory disease, a subject previously treated for an inflammatory disease, a subject with a family history of inflammatory disease, or a subject predisposed to an inflammatory disease.

The methods to treat, alleviate, ameliorate, relieve, delay onset of, inhibit progression of, reduce severity of, or reduce incidence of one or more symptoms of a non-cancer-related chronic inflammatory disease in a subject can further include a strategy for improving the efficiency of nucleic acid-based expression of p62 in subjects. The strategy can include a self-replicating viral replicon, codon optimization, in vivo electroporation, incorporation of a CpG stimulatory motif, including a sequence for targeting of the endocytic or ubiquitin-processing pathways, including a Marek's disease virus type 1 VP22 sequence, a prime-boost regimen, a mucosal delivery vector, and a nucleic acid delivery system. The nucleic acid delivery system can be a polymer gene delivery system, a liposomal delivery system, and a cell-penetrating peptide gene delivery system.

Any of the above methods can further include administering an anti-inflammatory chemotherapeutic or biological agent. The chemotherapeutic agent can be a nonsteroidal anti-inflammatory drug, a glucocorticoid, methotrexate, cyclosporine, or rapamycin. The anti-inflammatory biological agent can be an anti-TNF antibody, an anti-IL1 antibody, an anti-IL6 antibody, an anti-IL6 receptor antibody, an anti-IL12/23 antibody, an anti-IL17 antibody, an anti-IL1R antibody, an anti-IL1 receptor antagonist, and a soluble IL-1 receptor.

Certain aspects and embodiments are described further in the following description, examples, claims and drawings.

BRIEF DESCRIPTION OF THE DRAWING

The drawings illustrate embodiments of the technology and are not limiting.

FIG. 1 shows a wild type nucleic acid sequence of human p62 (SEQ ID NO: 1);

FIG. 2 shows a wild type amino acid sequence of the human p62/SQSTM1 encoded by the nucleic acid sequence (SEQ ID NO: 2);

FIG. 3 shows a cartoon of the domain structure of human p62/SQSTM1;

DETAILED DESCRIPTION OF THE INVENTION

Figure 4:
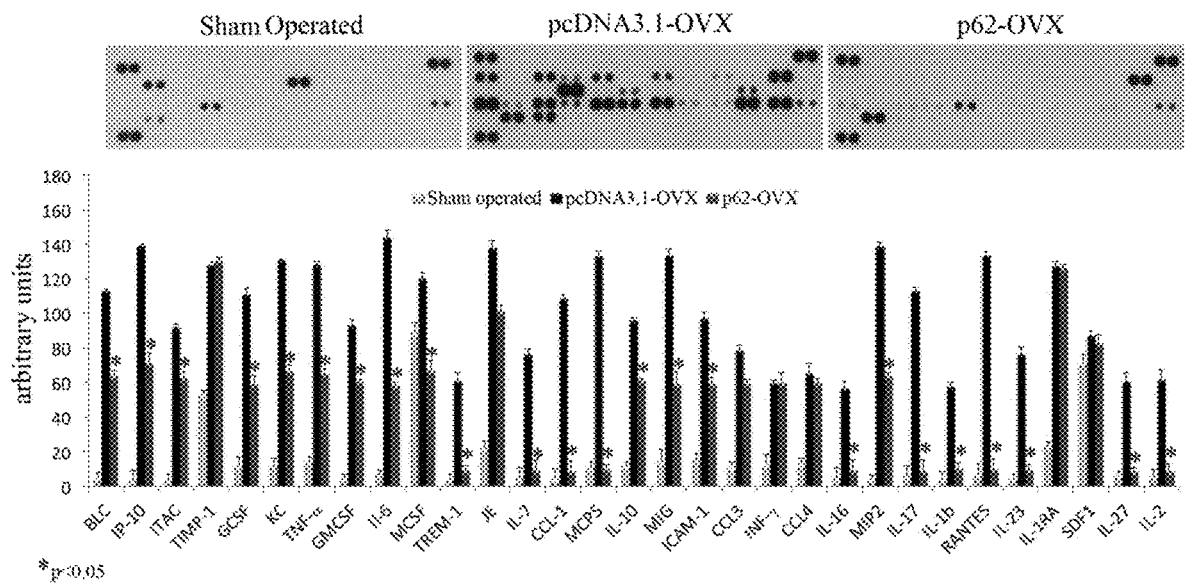
FIG. 4 shows the effect of p62/SQSTM1 DNA introduction on the prevention of osteoporosis in a mouse model for osteoporosis.

Provided herein are p62 compositions and methods for treatment of chronic inflammation. The inventors have found that administering p62, such as a p62 encoding nucleic acid, to a subject suppresses generation of inflammatory cytokines. Consequently polynucleotides encoding a p62 polypeptide or, p62 polypeptides administered to a subject can be used to prevent and/or mitigate development of inflammation-associated diseases (the list of such diseases includes but is not limited to, osteoporosis, obesity, metabolic syndrome, type 2 diabetes, fat liver, inflammatory bowel disease, gastritis, chronic pancreatitis, asthma, chronic obstructive pulmonary disease (COPD), rheumatoid arthritis (RA), osteoarthritis, multiple sclerosis (MS), psoriasis, congestive heart failure (CHF), atherosclerosis, neurodegenerative diseases (ALS, Parkinson, Alzheimer's, Huntington disease), gout, asbestosis and silicosis.

As used herein, "p62 polypeptide" means a polypeptide corresponding to the full length p62/SQSTM1 protein. The term also includes all homologs, analogs, fragments or derivatives of the p62/SQSTM1 protein. In one embodiment, the isolated p62 polypeptide has an amino acid sequence as shown in FIG. 2 (SEQ ID NO: 2). A "p62 encoding nucleic acid" means a DNA or RNA that encodes at least a portion of a p62 polypeptide or variant.

In some embodiments, the subject is a human. In other embodiments, the subject is a non-human mammal including, but not limited to, a horse, cow, sheep, pig, deer, dog, cat, rat, or a mouse.

TABLE 1 p62/SQSTM1 of Various Species

| Species | SEQ ID NO | Polypeptide Accession No |
|---|---|---|
| Human | 2 | NP_003891.1 |
| Domestic cow | 3 | AAI08088.1 |
| Common marmoset | 4 | XP_002744508.1 |
| Domestic dog | 5 | XP_005626405.1 |
| White rhinoceros | 6 | XP_004428485.1 |
| Star-noised mole | 7 | XP_004693731.1 |
| Nine-banded armadillo | 8 | XP_004478189.1 |
| Lesser hedgehog tenrec | 9 | XP_004696907.1 |
| Elephant shrew | 10 | XP_006898178.1 |
| Domestic cat | 11 | XP_003980695.1 |
| Gorilla | 12 | XP_004043182.1 |
| Naked mole rat | 13 | XP_004836787.1 |
| Thirteen-lined ground squirrel | 14 | XP_005339398.1 |
| Lesser Egyptian jerboa | 15 | XP_004666668.1 |
| West Indian Ocean coelacanth | 16 | XP_005995405.1 |
| Crab-eating macaque | 17 | XP_005558842.1 |
| Rhesus macaque | 18 | AFE80687.1 |
| Golden hamster | 19 | XP_005071915.1 |
| Prairie vole | 20 | XP_005350213.1 |
| House mouse | 21 | NP_035148.1 |
| American pika | 22 | XP_004599535.1 |
| Degu | 23 | XP_004629477.1 |

TABLE 1-continued p62/SQSTM1 of Various Species

| Species | SEQ ID NO | Polypeptide Accession No |
|---|---|---|
| Walrus | 24 | XP_004412727.1 |
| King cobra | 25 | ETE69498.1 |
| Killer whale | 26 | XP_004284096.1 |
| Northern greater galago | 27 | XP_003799205.1 |
| Sheep | 28 | ACR56704.1 |
| Bonobo | 29 | XP_003809255.1 |
| Common chimpanzee | 30 | XP_001153075.1 |
| Olive baboon | 31 | XP_003900678.1 |
| Sumatran orangutan | 32 | NP_001125548.1 |
| Common rat | 33 | NP_787037.2 |
| Bolivian squirrel monkey | 34 | XP_003943999.1 |
| Florida manatee | 35 | XP_004387215.1 |

In addition to the full length amino acid sequence or the polypeptide encoding nucleic acid thereof, the polypeptides of the present invention may also include fragments or truncations, analogs, and homologs of the p62 polypeptide and truncations thereof as described herein. Fragments can include peptides (or encode peptides) of at least 5, at least 10, at least 15, at least 20, at least 25, at least 30, at least 50, at least 100, at least 200 or at least 300 amino acid residues of the full length polypeptide.

Deletions of one or more amino acids, or discrete portions from the amino acid sequence of the p62/SQSTM1 protein are also included. The deleted amino acids may or may not be contiguous. The lower limit length of the resulting analog with a deletion mutation is about 10, about 20, about 50, or about 100 amino acids.

In some embodiments, the p62 polypeptide (or a nucleic acid encoding for the polypeptide) has one or more deleted domains. While not wishing to be held by theory, the inventors hold that the deletion of one or more domains of the p62 polypeptide provide a more compact and manipulable polypeptide for directing an immune response. For example, by disrupting or eliminating one or more of the domains of a p62 polypeptide, anti-inflammatory effect can be retained (or improved if the deleted or disrupted domain does not contribute to this effect) in a more compact molecule, and potentially increase per weight basis.

The p62 polypeptide has a domain structure as provided in Table 2 below and as shown in FIG. 3:

TABLE 2 p62 Polypeptide Domain Structure

| Domain/site | Full name | Location | Description |
|---|---|---|---|
| PB1 | Phox/Bem1p domain (=OPR domain) | 20-102 | PB1-domain is conserved among eukaryotes (protista, plants, fungi and animals). PB1- domain has specific - ubiquitin-like beta-grasp fold. There are 3 types of PB1-domains: type I domains contains acid OPCA-motif, type II domains contain conservative Lys residue in the first beta-sheet, and I/II type domains contain both of the above. OPCA-motif can bind to basic amino acids (e.g., lysine) via salt bridges, enabling ability of PB1-domains to form heteromeric structures (Sumimoto et al., 2007). PB1-domain of p62 is type I/II (Lamark et al., 2003). PB1-domain is responsible for di- and multimerization of p62, as well as interaction with other proteins: MEKK3, MEK5, PKCζ, PKC-lambda/ι (protein kinases containing PB1-domain), NBR1 (Next to BRCA1, contains PB1-domain) (Nezis, Stenmark, 2011). |

TABLE 2-continued p62 Polypeptide Domain Structure

| Domain/site | Full name | Location | Description |
|---|---|---|---|
| ZZ | Zn2+-finger ZZ type | 122-167 | ZZ- domain is $Zn^{2+}$-finger of C2H2 type. ZZ-domain of p62 binds to RIP1 (receptor interacting protein 1). RIP1 is a regulatory protein kinase which integrates signaling pathways activated by bacterial or viral infection (via PAMP), death receptors, or genotoxins; it takes part in determination of cell fate (survival, apoptosis, or necrosis) (Festjens et al., 2007). |
| NLS2 | Nuclear localization signal 2 | 183-194 | Tentative nuclear localization signal (Pankiv et al., 2009) |
| TBS | TRAF6-binding domain | 228-233 | p62 binds via TB domain to E3-ubiquitin protein ligase TRAF6. TRAF6 activates kinase TAK1, polyubiqitinating it via K63). TRAF6 participates in signaling from RANK-L, IL-1R, TCR, BCR and TGFbeta receptors (Landström, 2010). Interaction of p62 with TRAF6 stimulates autoubiqitination of TRAF6 nu E3- ligase activity. This process requires PB1- and UBA-domains (Moscat et al., 2006). |
| NLS1 | Nuclear localization signal 1 | 261-273 | Tentative nuclear localization signal (Pankiv et al., 2009) |
| NES | Nuclear export signal | 303-321 | Tentative nuclear export signal (Pankiv et al., 2009) |
| LIR | LC3 interaction region | 321-342 | LIR-domain is required for binding of p62 to LC3 protein (wild-type human microtubule-associated protein 1 light chain 3, Light Chain 3) (Pankiv et al., 2007). LC3 -ubiquitin-like protein, conjugating with phosphatidyl ethanolamine of autophagosome membrane (Tanida, 2011). P62 via interaction of with LC3, p62 is recruited to autophagosomes (Shvets et al., 2011), apparently transporting ubiquitinated proteins associated with UBA domain. |
| KIR | Keap1 interaction region | 343-357 | KIR domain is required for interaction with DC domain of Keap1 protein, containing Kelch repeats (Komatsu et al., 2010). Keap1 (Kelch-like ECH-associated protein 1) is a regulator of activity of transcription factor Nrf2 (NF-E2-related factor 2). Nrf2 regulates expression of genes involved in glutathione synthesis, ROS detoxification, metabolism of xenobiotics and drug transport (Taguchi et al., 2011). Overexpression of p62 displaces Nrf2 from Keap1, Nrf2 is stabilized which lead to stimulation of expression of Nrf2-dependent genes. Paradoxically, hyperactivation of Nrf2 and overexpression of genes considered "cytoprotective" causes severe pathology (Komatsu et al., 2010). |
| PEST | | 267-283 346-380 | Targets of proteosomal degradation (Okazaki et al. 1999. Cloning, Expression Profile, and Genomic Organization of the Mouse STAP/A170 Gene. Genomics 60: 87-95) |
| UBA | Ubiquitin-associated domain | 389-434 | UBA-domain is one of the domains which can bind to polyubiquitinated labels (along with CUE, UIM, NZF etc.). UBA-domains can be divided in four classes depending on their ability to bind polyubiquitin labels of different structures (K6, K29, K48, K63). UBA-domain of p62 belongs to class 4, which consists of domains with equal affinity for binding to K6, K29, K48, K63 (Raasi et al., 2005). UBA domain also participates in p62 dimerization (Garner et al., 2011). Most of the mutations associated with Paget disease are localized in UBA domain (Yan Jenny Chung, Van Hul, 2011). However, p62 mutations are not enough for osteoblasts to acquire the specific Paget phenotype: The expression of nucleocapsid protein of measles virus is also required (Singer, 2011). The structure of the UBA domain is known (Isogai et al., 2011). | p62 NCBI reference sequence: NP_003891 (sequestosome-1 isoform 1 [*Homo sapiens*]).

In some embodiments, one or more of the above domains are deleted from a human p62 polypeptide at corresponding codons for the nucleic acid regions of the p62 nucleic acid (in-frame deletions), as presented below.

TABLE 3

Deletions in p62

| Deleted domain | Start of the deletion, between nts | End of the deletion, between nts |
|---|---|---|
| PB1 | 1 and 20 | 102 and 122 |
| ZZ | 102 and 122 | 167 and 183 |
| NLS2 | 167 and 183 | 194 and 228 |
| TB | 194 and 228 | 233 and 261 |
| NLS1 | 233 and 261 | 273 and 303 |
| NES-LIR-KIR | 273 and 303 | 357 and 389 |
| UBA | Stop codon between 357 and 389 | Not applicable |

Nucleotide numbers refer to p62 NCBI reference sequence NP_003891 (sequestosome-1 isoform 1 [*Homo sapiens*]).

For example, any deletion of the encoding nucleic acid sequence that starts at nucleotide 102 up to nucleotide 122 and ends at 167 up to 183 is considered a ZZ deletion. Therefore, e.g. a deletion of nucleotides 110-175 is a ZZ deletion. Techniques for creating in-frame deletions are well known to those skilled in the art.

As used herein, "biologically active" refers to polypeptides according to the present invention having a similar structural function (but not necessarily to the same degree), and/or similar regulatory function (but not necessarily to the same degree), and/or similar biochemical function (but not necessarily to the same degree) as the individual wild type polypeptides.

As used herein, a "deletion" is defined as a change in the nucleotide or amino acid sequence in which one or more nucleotide or amino acid residues are absent as compared to the wild-type polynucleotide or polypeptide, respectively.

As used herein an "insertion" or "addition" is a change in the nucleotide or amino acid sequence that has resulted in the addition of one or more nucleotide or amino acid residues as compared to the wild-type polynucleotide or polypeptide, respectively.

As used herein "substitution" results from the replacement of one or more nucleotides or amino acids by different nucleotides or amino acids, respectively, as compared to the wild-type polynucleotide or polypeptide, respectively. In some embodiments, the amino acid substitution mutation is C145R or Q418R.

As used herein, the term "variant" means any polypeptide (including polypeptides encoded by the corresponding nucleic acid) having a substitution of, deletion of or addition of one (or more) amino acid from or to the sequence (or any combination of these), including allelic variations, as compared with the wild-type polypeptide. In some embodiments, the resultant polypeptide retains at least 75%, 80%, 85%, 90%, 95%, 99% or more of the biological activity as compared to the wild-type polypeptides as used in the present invention. Variants of the p62 polypeptides (including polypeptides encoded by the corresponding nucleic acid) can have at least 80%, at least 85%, at least 90%, at least 91%, at least 92%, at least 93%, at least 94%, at least 95%, at least 96%, at least 97%, at least 98%, or at least 99% sequence identity to any of the amino acid sequences listed in Table 1.

Sequence identity or homology can be determined using standard techniques known in the art, such as the Best Fit sequence program described by Devereux et al., Nucl. Acid Res. 12:387-395 (1984) or the BLASTX program (Altschul et al., J Mol. Biol. 215:403-410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids. Consequently, variants of the p62 polypeptides (including polypeptides encoded by the corresponding nucleic acid) can have at least 80%, at least 85%, at least 90%, at least 91%, at least 92%, at least 93%, at least 94%, at least 95%, at least 96%, at least 97%, at least 98%, or at least 99% sequence homology to any of the polypeptide sequences listed in Table 1

In some embodiments, variants or derivatives of the polypeptides of the present invention maintain the hydrophobicity/hydrophilicity of the amino acid sequence. Conservative amino acid substitutions are known in the art and may be made, for example from 1, 2 or 3 to 10, 20 or 30 substitutions. Amino acid substitutions may include the use of non-naturally occurring analogues, for example to increase blood plasma half-life.

The term "derivative" as used herein in relation to the amino acid sequence means chemical modification of a polypeptide of the invention.

Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a polypeptide conjugated with a polymer such as polyethylene glycol (PEG), or addition of PEG during chemical synthesis of a polypeptide of the invention.

Modifications of polypeptides or portions thereof can also include reduction/alkylation, chemical coupling to an appropriate carrier, or mild formalin treatment.

The term "post-translationally modified" or "modified" refers to any modification of an amino acid after its incorporation into a polypeptide chain. The term encompasses, but is not limited to, co-translational in vivo modifications, post-translational in vivo modifications, and post-translational in vitro modifications.

Other derivatives of the polypeptides of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylations site(s) are added or glycosylation sites are deleted or disabled. Furthermore, if no glycosylation is desired, the proteins can be produced in a prokaryotic host expression system.

Variants and/or derivatives of the polypeptides of the invention can be prepared by chemical synthesis or by using site-directed mutagenesis (Gillman et al., Gene 8:81 (1979); Roberts et at, Nature 328:731 (1987) or Innis (Ed.), 1990, PCR Protocols: A Guide to Methods and Applications, Academic Press, New York, N.Y.) or the polymerase chain reaction (PCR) method (Saiki et al, Science 239:487 (1988)), as exemplified by Daugherty et at (Nucleic Acids Res. 19:2471 (1991)) to modify nucleic acids encoding the p62 polypeptides of invention.

In another embodiment, polypeptides of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In order to enhance stability and/or reactivity, the polypeptides of the present invention can also be modified to incorporate one or more polymorphisms in the amino acid sequence resulting from natural allelic variation. Additionally, D-amino acids, non-natural amino acids or non-amino acid analogues can be substituted or added to produce a modified p62 polypeptide within the scope of this invention.

The polypeptides of the present invention may be produced by expression of a nucleotide sequence coding for same in a suitable expression system.

In addition, or in the alternative, the polypeptides can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic polypeptides may be confirmed by amino acid analysis or sequencing (e.g., the Edman degradation procedure). Additionally, the amino acid sequence of a p62 polypeptide, or any part thereof, may be altered during direct synthesis and/or combined using chemical methods with a sequence from other subunits, or any part thereof, to produce a variant polypeptide.

As used herein, the term "fusion proteins" refers to chimeric proteins comprising amino acid sequences of two or more different proteins. Typically, fusion proteins result from in vitro recombinant techniques well known in the art.

In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath J (1992) Protein Expr Purif 3-.26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and the protein is useful to facilitate purification.

Additional fusion expression vectors include pGEX (Pharmacia, a Piscataway, N.J.), pMAL (New England Biolabs, Beverly, Mass.) and pRITS (GE Healthcare Biosciences, Piscataway, N.J.) which fuse glutathione S transferase (GST), maltose B binding protein, or protein A, respectively, to the target recombinant protein. EBV, BKV, and other episomal expression vectors (ThermoFisher Scientific) can also be used.

In another aspect of the invention, p62 polypeptides can be non-covalently linked to a transport moiety or transfection agent. An example of a non-covalently linked peptide transfection agent is the Chariot protein delivery system (See U.S. Pat. No. 6,841,535; Morris et al. (1999) J. Biol. Chem. 274(35):24941-24946; and Morris et al. (2001) Nature Biotech. 19:1173-1176).

In certain embodiments, a nucleic acid molecule encoding p62 polypeptide is utilized. The nucleic acid molecule may comprise or consist of a nucleotide sequence encoding one or more p62 polypeptides, or fragments (including fragments that code for domains in any order or polypeptides wherein one or more domains are deleted or disrupted) or derivatives thereof, such as that contained in a DNA insert in an ATCC Deposit. Variants of the p62 a nucleic acid molecules encoding p62 polypeptide can have at least 80%, at least 85%, at least 90%, at least 91%, at least 92%, at least 93%, at least 94%, at least 95%, at least 96%, at least 97%, at least 98%, or at least 99% sequence identity to SEQ ID NO: 1.

The term "nucleic acid sequence" or "nucleic acid molecule" refers to a DNA or RNA sequence. The term encompasses molecules formed from any of the known base analogs of DNA and RNA such as, but not limited- to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5' methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

In certain embodiments of the present invention, vectors are used to transfer a polynucleotide encoding a polypeptide to a cell. A vector is any molecule used to transfer a nucleic acid sequence to a host cell. In certain cases, an expression vector is utilized. An expression vector is a nucleic acid molecule that is suitable for introduction to and/or propagation in a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence can be located upstream or downstream from the coding sequence and affect transcription of the sequence. In certain embodiments, the flanking sequence is a transcriptional regulatory region that drives high-level gene expression in the target cell. The transcriptional regulatory region can include, for example, a promoter, enhancer, silencer, repressor element, or combinations thereof. The transcriptional regulatory region can be constitutive, tissue-specific, cell-type specific (i.e., the region is drives higher levels of transcription in a one type of tissue or cell as compared to another), or regulatable (i.e., responsive to interaction with a molecule). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions can be utilized.

Suitable transcriptional regulatory regions include, for example, the CMV promoter (i.e., the CMV-immediate early promoter); promoters from eukaryotic genes (i.e., the estrogen-inducible chicken ovalbumin gene, the interferon genes, the gluco-corticoid-inducible tyrosine aminotransferase gene, and the thymidine kinase gene); and the major early and late adenovirus gene promoters; the SV40 early promoter region (Bernoist and Chambon, 1981, Nature 290: 304-10); the promoter contained in the 3' long terminal repeat (LTR) of Rous sarcoma virus (RSV) (Yamamoto, et al., 1980, Cell 22:787-97); the herpes simplex virus thymidine kinase (HSV-TK) promoter (Wagner et al., 1981, Proc. Natl. Acad. Sci. U.S.A. 78:1444-45); the regulatory sequences of the metallothionine gene (Brinster et al., 1982, Nature 296:39-42); prokaryotic expression vectors such as the beta-lactamase promoter (VIIIa-Kamaroff et al., 1978, Proc. Natl. Acad. Sci. U.S.A., 75:3727-31); or the tac promoter (DeBoer et al., 1983, Proc. Natl. Acad. Sci. U.S.A., 80:21-25). Tissue- and/or cell-type specific transcriptional control regions include, for example, the elastase I gene control region which is active in pancreatic acinar cells (Swift et al., 1984, Cell 38:639-46; Ornitz et al., 1986, Cold Spring Harbor Symp. Quant. Biol. 50:399-409 (1986); MacDonald, 1987, Hepalology 7:425-515); the insulin gene control region which is active in pancreatic beta cells (Hanahan, 1985, Nature 315:115-22); the immunoglobulin gene control region which is active in lymphoid cells (Grosschedl et al., 1984, Cell 38:647-58; Adames et al., 1985, Nature 318:533-38; Alexander et al., 1987, Mol. Cell. Biol., 7:1436-44); the mouse mammary tumor virus control region intesticular, breast, lymphoid and mast cells (Leder et al., 1986, Cell 45:485-95); the albumin gene control region, in liver (Pinkert et al., 1987, Genes and Devel. 1:268-76); the alpha-feto-protein gene control region in liver (Krumlauf et al., 1985, Mol. Cell. Biol., 5:1639-48; Hammer et al., 1987, Science 235:53-58); the alpha 1-antitrypsin gene control region in liver (Kelsey et al., 1987, Genes and Devel. 1:161-71); the beta-globin gene control region in myeloid cells (Mogram et al., 1985, Nature 315:338-40; Kollias et al., 1986, Cell 46:89-94); the myelin basic protein gene control region in oligodendrocyte cells in the brain (Readhead et al., 1987, Cell 48:703-12); the myosin light chain-2 gene control region in skeletal muscle (Sani, 1985, Nature 314:283-86); the gonadotropic releasing hormone gene control region in the hypothalamus (Mason et al., 1986, Science 234:1372-78), and the tyrosinase promoter in melanoma cells (Hart, I. Semin Oncol 1996 February; 23(1):154-8; Siders, et al. Cancer Gene Ther 1998 September-October; 5(5):281-91), among others. Inducible promoters that are activated in the presence of a certain molecule or condition such as light, heat, radiation, tetracycline, or heat shock proteins, for example, can also be used (see, for example, WO 00/10612). Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

In some embodiments of the invention, provided herein are vaccines that include a p62 polynucleotide or p62 polypeptide. Such vaccines can further include an adjuvant. Any of a variety of adjuvants can be employed in the vaccines of this invention to enhance the immune response. Most adjuvants contain a substance designed to protect the antigen from rapid catabolism, such as aluminum hydroxide or mineral oil, and a nonspecific stimulator of immune responses. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Suitable adjuvant types include, but are not limited to, gel-type, microbial, particulate, oil-emulsion, surfactant-based, and synthetic adjuvants.

In certain embodiments, it may be advantageous to combine a p62 polypeptide or polynucleotide encoding a p62 polypeptide, or derivative thereof, with one or more co-stimulatory component(s) such as cell surface proteins, cytokines, chemokines, or signaling molecules in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. Nature 1999, 397: 263-265;

Peach, et al. J Exp Med 1994, 180: 2049-2058) such as the CD28 binding polypeptides B7.1 (CD80; Schwartz, 1992; Chen et al, 1992; Ellis, et al. J. Immunol., 156(8): 2700-9) and B7.2 (CD86; Ellis, et al. J. Immunol., 156(8): 2700-9); polypeptides which bind members of the integrin family (i.e., LFA-1 (CD11a/CD18); Sedwick, et al. J Immunol 1999, 162: 1367-1375; Wulfing, et al. Science 1998, 282: 2266-2269; Lub, et al. Immunol Today 1995, 16: 479-483) including members of the ICAM family (i.e., ICAM-1, -2 or -3); polypeptides which bind CD2 family members (i.e., CD2, signaling lymphocyte activation molecule (CDw150 or "SLAM"; Aversa, et al. J Immunol 1997, 158: 4036-4044)) such as CD58 (LFA-3; CD2 ligand; Davis, et al. Immunol Today 1996, 17: 177-187) or SLAM ligands (Sayos, et al. Nature 1998, 395: 462-469); polypeptides which bind heat stable antigen (HSA or CD24; Zhou, et al. Eur J Immunol 1997, 27: 2524-2528); polypeptides which bind to members of the TNF receptor (TNFR) family (i.e., 4-1BB (CD137; Vinay, et al. Semin Immunol 1998, 10: 481-489), OX40 (CD134; Weinberg, et al. Semin Immunol 1998, 10: 471-480; Higgins, et al. J Immunol 1999, 162: 486-493), and CD27 (Lens, et al. Semin Immunol 1998, 10: 491-499)) such as 4-1BBL (4-1BB ligand; Vinay, et al. Semin Immunol 1998, 10: 481-48; DeBenedette, et al. J Immunol 1997, 158: 551-559), TNFR associated factor-1 (TRAF-1; 4-1BB ligand; Saoulli, et al. J Exp Med 1998, 187: 1849-1862, Arch, et al. Mol Cell Biol 1998, 18: 558-565), TRAF-2 (4-1BB and OX40 ligand; Saoulli, et al. J Exp Med 1998, 187: 1849-1862; Oshima, et al. Int Immunol 1998, 10: 517-526, Kawamata, et al. J Biol Chem 1998, 273: 5808-5814), TRAF-3 (4-1BB and OX40 ligand; Arch, et al. Mol Cell Biol 1998, 18: 558-565; Jang, et al. Biochem Biophys Res Commun 1998, 242: 613-620; Kawamata S, et al. J Biol Chem 1998, 273: 5808-5814), OX40L (OX40 ligand; Gramaglia, et al. J Immunol 1998, 161: 6510-6517), TRAF-5 (OX40 ligand; Arch, et al. Mol Cell Biol 1998, 18: 558-565; Kawamata, et al. J Biol Chem 1998, 273: 5808-5814), and CD70 (CD27, ligand; Couderc, et al. Cancer Gene Ther., 5(3): 163-75). CD154 (CD40 ligand or "CD40L"; Gurunathan, et al. J. Immunol., 1998, 161: 4563-4571; Sine, et al. Hum. Gene Ther., 2001, 12: 1091-1102) may also be suitable.

Additional strategies for improving the efficiency of nucleic acid-based immunization may also be used including, for example, the use of self-replicating viral replicons (Caley, et al. 1999. Vaccine, 17: 3124-2135; Dubensky, et al. 2000. Mol. Med. 6: 723-732; Leitner, et al. 2000. Cancer Res. 60: 51-55), codon optimization (Liu, et al. 2000. Mol. Ther., 1: 497-500; Dubensky, supra; Huang, et al. 2001. J. Virol. 75: 4947-4951), in vivo electroporation (Widera, et al. 2000. J. Immunol. 164: 4635-3640), incorporation of CpG stimulatory motifs (Gurunathan, et al. Ann. Rev. Immunol., 2000, 18: 927-974; Leitner, supra; Cho, et al. J. Immunol. 168(10):4907-13), sequences for targeting of the endocytic or ubiquitin-processing pathways (Thomson, et al. 1998. J. Virol. 72: 2246-2252; Velders, et al. 2001. J. Immunol. 166: 5366-5373), Marek's disease virus type 1 VP22 sequences (J. Virol. 76(6):2676-82, 2002), prime-boost regimens (Gurunathan, supra; Sullivan, et al. 2000. Nature, 408: 605-609; Hanke, et al. 1998. Vaccine, 16: 439-445; Amara, et al. 2001. Science, 292: 69-74), and the use of mucosal delivery vectors such as Salmonella (Darji, et al. 1997. Cell, 91: 765-775; Woo, et al. 2001. Vaccine, 19: 2945-2954). Other methods are known in the art, some of which are described below.

Nucleic acids encoding p62 polypeptides can be administered to subjects by any of several available techniques. Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors can be constructed using standard recombinant techniques widely available to one skilled in the art. Many such techniques are disclosed in Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), and PCR Protocols: A Guide to Methods and Applications (Innis, et al. 1990. Academic Press, San Diego, Calif.).

Suitable retroviral vectors include derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include .PSI.2, PA317 and PA12, among others. The vector virions produced using such cell lines can be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, Hum. Gene Ther., 5 (3): 343-79; Culver, K., et al., Cold Spring Harb. Symp; Quant. Biol., 59: 685-90); Oldfield, E., 1993, Hum. Gene Ther., 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors are useful for gene transfer into eukaryotic cells (Rosenfeld, M., et al., 1991, Science, 252 (5004): 431-4; Crystal, R., et al., 1994, Nat. Genet., 8 (1): 42-51). Routes for administrating recombinant adenovirus to different tissues in vivo have included intratracheal instillation (Rosenfeld, M., et al., 1992, Cell, 68 (1): 143-55) injection into muscle (Quantin, B., et al., 1992, Proc. Natl. Acad. Sci. U.S.A., 89 (7): 2581-4), peripheral intravenous injection (Herz, J., and Gerard, R., 1993, Proc. Natl. Acad. Sci. U.S.A., 90 (7): 2812-6) and stereotactic inoculation to brain (Le Gal La Salle, G., et al., 1993, Science, 259 (5097): 988-90), among others.

Adeno-associated virus (AAV) demonstrates high-level infectivity, broad host range and specificity in integrating into the host cell genome (Hermonat, P., et al., 1984, Proc. Natl. Acad. Sci. U.S.A., 81 (20): 6466-70). Herpes Simplex Virus type-1 (HSV-1) is yet another attractive vector system, especially for use in the nervous system because of its neurotropic property (Geller, A., et al., 1991, Trends Neurosci., 14 (10): 428-32; Glorioso, et al., 1995, Mol. Biotechnol., 4 (1): 87-99; Glorioso, et al., 1995, Annu. Rev. Microbiol., 49: 675-710).

Poxvirus is another useful expression vector (Smith, et al. 1983, Gene, 25 (1): 21-8; Moss, et al, 1992, Biotechnology, 20: 345-62; Moss, et al, 1992, Curr. Top. Microbiol. Immunol., 158: 25-38; Moss, et al. 1991. Science, 252: 1662-1667). Poxviruses shown to be useful include vaccinia, NYVAC, avipox, fowlpox, canarypox, ALVAC, and ALVAC (2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively ALVAC-based recombinant viruses (i.e., ALVAC-1 and ALVAC-2) are also suitable vectors (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in practicing the present invention. Suitable plasmid vectors are compatible with bacterial, insect, and/or mammalian host cells. Such vectors include, for example, PCR-II, pCR3, and pcDNA3.1 (ThermoFisher), pBSII(Agilent Technology Santa Clara Calif. pET15 (EMD Millipore, Bullerica, Mass.) pGEX (GE HealthCare Bioscience, Piscataway, N.J.), pEGFP-N2 (Clontech, Palo Alto, Calif.), pETL (BlueBacII, Thermofisher), pDSR-alpha (PCT pub. No. WO 90/14363) and pFastBacDual (ThermoFisher)) as well as Bluescript® plasmid derivatives (a high copy number COLE1-based phagemid, (Agilent Technology Santa Clara, Calif.), PCR cloning plasmids designed for cloning Taq-amplified PCR products (e.g., TOPO™ TA Cloning®. kit, PCR2.1® plasmid derivatives, Thermofisher Bacterial vectors may also be used with the current invention. These vectors include, for example, *Shigella, Salmonella, Vibrio cholerae, Laclobacillus, Bacille calmette guerin* (BCG), and *Streptococcus* (see for example, WO 88/6626; WO 90/0594; WO 91/13157; WO 92/1796; and WO 92/21376). Many other non-viral plasmid expression vectors and systems are known in the art and could be used with the current invention.

Suitable nucleic acid delivery techniques include DNA-ligand complexes, adenovirus-ligand-DNA complexes, direct injection of DNA, CaPO4 precipitation, gene gun techniques, electroporation polymer gene delivery system, cell-penetrating peptide gene delivery system, and colloidal dispersion systems, among others. Polymer gene delivery system includes polyetherimide- and pluronic-based delivery systems. Cell-penetrating peptide-based systems include 9-35 mer cationic and/or amphipathic peptides capable of mediating translocation of DNA across plasma membrane. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles useful as delivery vehicles in vitro and in vivo. RNA, DNA and intact virions can be encapsulated within the aqueous interior and be delivered to cells in a biologically active form (Fraley, R., et al., 1981, Trends Biochem. Sci., 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. The lipid can be a diacylphosphatidylglycerol. The, lipid moiety of diacylphosphatidylglycerol can have 14-18 carbon atoms. The lipid moiety of diacylphosphatidylglycerol can have 16-18 carbon atoms. The lipid moiety of diacylphosphatidylglycerol can be saturated. Illustrative phospholipids include egg phosphatidylcholine, phosphatidylethanolamine, sphingolipids, cerebrosides, and gangliosides.

In an embodiment, a method for the treatment of inflammatory diseases is provided. In various embodiments, the method for the treatment of inflammatory diseases that are not related to cancer is provided. In some embodiments, the treatment of inflammatory diseases comprises administering a therapeutically effective amount of p62 polypeptides or p62 encoding nucleic acids to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of inflammatory diseases.

In one aspect of the invention, a method for administering p62 polypeptides or p62 encoding nucleic acids to a subject suffering from inflammatory disease or relapse is provided. In some embodiments, p62 polypeptides or p62 encoding nucleic acids are administered to a subject in such amounts and for such time as is necessary to achieve the desired result (i.e. treatment of inflammatory disease). In certain embodiments of the present invention a "therapeutically effective amount" of p62 polypeptides and p62 encoding nucleic acids is that amount effective for treating, alleviating, ameliorating, relieving, delaying onset of, inhibiting progression of, reducing severity of, and/or reducing incidence of one or more symptoms or features of inflammatory disease. In some embodiments, the p62 polypeptides or p62 encoding nucleic acids of the invention are administered to a subject previously treated for inflammatory disease. In some embodiments, the p62 polypeptides or p62 encoding nucleic acids of the invention are administered to a subject with a family history of inflammatory disease. In some embodiments, the p62 polypeptides or p62 encoding nucleic acids of the invention are administered to a subject with a predisposition for inflammatory diseases. For example, a subject who is genetically predisposed to inflammatory diseases (ALS, Parkinson disease, Huntington disease), or subjected to environmental factors provoking inflammatory disease (e.g., tobacco smoke, asbestos, silica particles). Genetic predisposition to ALS is associated with mutations in genes of superoxidismutase or TAR DNA-binding protein 43

(TDP-43). Genetic predisposition to Parkinson disease is associated with the parkin and synuclein genes. Genetic predisposition to Huntington disease is associated with a mutation in huntingtin gene (Glass, C. K., K. Saijo, et al. (2010). "Mechanisms Underlying Inflammation in Neurodegeneration." Cell 140(6): 918-934). Tobacco smoke, asbestos, silica particles are all well-known inducers of chronic inflammation as persistent allergens and undigestable forein particles; they lead to chronic obstructive pulmonary disease, asbestosis and silicosis (Medzhitov 2010. Inflammation 2010: New Adventures of an Old Flame. Cell 140:771-776)

In some embodiments, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of an inflammatory disease, disorder, and/or condition. In some embodiments, the inflammatory disease, disorder, and/or condition is non-cancer-related. Such diseases include, but not limited to, osteoporosis, obesity, metabolic syndrome, type 2 diabetes, fat liver, inflammatory bowel disease, gastritis, chronic pancreatitis, asthma, chronic obstructive pulmonary disease (COPD), rheumatoid arthritis (RA), osteoarthritis, multiple sclerosis (MS), psoriasis, congestive heart failure (CHF), atherosclerosis, neurodegenerative diseases (ALS, Parkinson, Alzheimer's, Huntington disease), gout, asbestosis and silicosis.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of osteoporosis. Osteoporosis is the most common disease of the bone associated with bone loss and affecting mostly women after onset of menopause. Menopause leads to decrease in estrogen levels, thus ovariectomy in rodents leading to cessation of estrogen generation is the most common model for osteoporosis. Postmenopausal period is marked by elevation of cytokines such us IL-6, TNF-alpha and IL-1beta, and the same cytokines are elevated under ovariectomy. TNF and IL-1 have potent antiapoptotic effects in osteoclasts prolonging OC lifespan, accelerating bone resorption and inhibiting bone formation, and blockade of TNF-alpha and IL-1beta prevents osteoporosis due to estrogendeficiency. (Mundy 2007. Osteoporosis and Inflammation. Nutrition Reviews 65:S147-S151; Lencel and Magne 2011. Inflammaging: The driving force in osteoporosis? Medical Hypotheses 76:317-321).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of obesity, type 2 diabetes and fat liver disease. Obesity is increasingly prevalent in the population and strongly associated with the development of insulin resistance, an underlying feature of both type 2 diabetes (T2D) and metabolic syndrome. Insulin resistance has been recognized as the integral feature of metabolic syndrome, which includes glucose intolerance, insulin resistance, obesity, hypertriglyceridemia, low HDL cholesterol, hypertension, and accelerated atherosclerosis. Growing evidence links a chronic, subacute inflammatory state to the development of obesity and the coexisting conditions of insulin resistance, T2D and metabolic syndrome. The proinflammatory cytokine TNF-a has been demonstrated to mediate insulin resistance as a result of obesity in many rodent obesity models. In addition to TNF-alpha, various other inflammatory mediators and cytokines are also overexpressed in adipose and other tissues in experimental mouse models of obesity and in humans. Proinflammatory cytokines can cause insulin resistance and anti-inflammatory medications may reverse it suggesting that inflammation may be directly involved in its (Hotamisligil 2006. Inflammation and metabolic disorders. Nature 444:860-867).

Non-alcoholic fatty liver disease (NAFLD) is recognized as the hepatic manifestation of metabolic syndrome, and is characterized by the accumulation of fatty infiltrations affecting >5% of the liver. The clinical implications of NAFLD are derived by its potential to progress to steatohepatitis (NASH), fibrosis, cirrhosis, and in some cases, hepatocellular carcinoma. The prevalence of NAFLD is rising in parallel with the increasing rate of obesity, and this global trend is attributed to the diet of the Western lifestyle. The pathogenesis of NAFLD is not well understood, but is proposed to be a "two-hit" process. The first "hit" leads to lipid accumulation and steatosis. Mechanisms of this lipid accumulation are unclear, but likely involve dysregulated lipid homeostasis including beta-oxidation, very low density lipoprotein secretion, de novo lipogenesis, and lipid trafficking and storage. This hepatic steatosis sensitizes the liver to a "second hit" leading to inflammation, a key pathophysiologic feature of steatohepatitis, and progressive liver disease (Renaud et al. 2014. Effect of Diet on Expression of Genes Involved in Lipid Metabolism, Oxidative Stress, and Inflammation in Mouse Liver—Insights into Mechanisms of Hepatic Steatosis. PLoS ONE 9:e88584)

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of IBD, including, but not limited to ulcerative colitis and Crohn's disease. Inflammatory Bowel Disease (IBD) is a chronic inflammatory disorder of gastrointestinal tract. Examples of IBD include ulcerative colitis and Crohn's disease. Substantial evidence from human genetic studies and from preclinical IBD models suggests that failures by either the mucosal epithelial layer or the immune system to properly interact with the lumen microbial community may underlie the pathogenic processes. IBD is also an important risk factor for development of colon carcinoma, where proinflammatory cytokines TNFa, interleukin-1, IL-6 plays a significant role role (Danese and Mantovani 2010. Inflammatory bowel disease and intestinal cancer: a paradigm of the Yin-Yang interplay between inflammation and cancer. Oncogene 29:3313-3323)

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of asthma. Asthma is an inflammatory disease in the airway, leading to airway hyperresponsiveness, obstruction, mucus hyper-production and airway wall remodeling. Asthma is classically recognized as the typical Th2 disease, with increased IgE levels and eosinophilic inflammation in the airway. Emerging Th2 cytokines modulates the airway inflammation, which induces airway remodeling. However, the relatively simple paradigm has been doubted because of the realization that strategies designed to suppress Th2 function are not effective enough for all patients in the clinical trials. (Kudo et al. 2013. Pathology of asthma. Frontiers in Microbiology 4:263).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of COPD (chronic obstructive pulmonary disease). COPD is associated with chronic inflammation affecting predominantly lung parenchyma and peripheral airways and results in largely irreversible and progressive airflow limitation. This inflammation is characterized by increased numbers of alveolar macrophages, neutrophils, and T lymphocytes, which are recruited from the circulation. Oxidative stress plays a key role in driving this inflammation. The pulmonary inflammation may enhance the development and growth of lung cancer. The peripheral inflammation extends into the circulation, resulting in systemic inflammation with the same inflammatory proteins. Systemic inflammation may worsen comorbidities. Treatment of pulmonary inflammation may therefore have beneficial effects. (Barnes 2014. Cellular and Molecular Mechanisms of Chronic Obstructive Pulmonary Disease. Clinics in Chest Medicine 35:71-86).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of Rheumatoid Arthritis (RA). RA is a chronic, inflammatory, systemic autoimmune disease that affects about 1% of the general population in Western countries and is two to three times more common in women than in men. Although the etiology and pathogenesis of RA is not yet fully understood, the disease is characterized by aggressive synovial hyperplasia (pannus formation) and inflammation (synovitis), which, if left untreated, leads to progressive destruction of joint cartilage and bone. The destructive lesions result from immune responses and nonantigen-specific innate inflammatory processes.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of osteoarthritis (OA) is a disease of the joints that affects several million individuals worldwide. This disease, which involves mainly the diarthrodial joints, is chronic and develops slowly over decades. The role of synovial inflammation in the pathophysiology of OA is now widely accepted. Synovitis has been considered secondary to the cartilage changes yet findings indicate that synovial inflammation could be a component of the early events leading to the clinical stage of OA. Synovial inflammation leads to the production and release of pro-inflammatory cytokines and several other inflammatory mediators. Some of these factors, including the pro-inflammatory cytokines, diffuse through the synovial fluid into the cartilage, where they activate chondrocyte production of the catabolic factors through auto- and paracrine mechanisms.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of Multiple Sclerosis (MS). MS is characterized by inflammation, demyelination, and axon degeneration in the CNS. Individuals are plagued by MS-associated comorbidities, such as chronic pain, fatigue, depression, sleep disorders, spasticity, gait and coordination imbalances, migraines, sensory organ dysfunctions, and overall cognitive impairment (Damal et al. 2013. Optimizing therapeutics in the management of patients with multiple sclerosis: a review of drug efficacy, dosing, and mechanisms of action. Biologics 7:247-258). This pathology results from a primary defect in the immune system that targets components of the myelin sheath, resulting in secondary effects on neurons. MS is considered an immune-mediated disease characterized by the presence of inflammatory demyelinating lesions in the CNS. Infection by bacteria or viruses or other environmental stimuli trigger the activation of microglia and astrocytes in multiple sclerosis (MS), leading to the production of proinflammatory cytokines through activation of the transcription factors NF-kappa-B and AP-1 (Luessi et al. 2012. Neurodegeneration in multiple sclerosis: novel treatment strategies. Expert Rev Neurother 12:1061-1076).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of atherosclerosis. Atherosclerosis shares features with traditional inflammatory diseases including rheumatoid arthritis. Atherosclerosis is the main cause of coronary artery and cerebrovascular disease, which are the leading cause of death worldwide. Atherogenesis is thought to begin with the development of endothelial dysfunction caused by the exposure of the vessel wall to systemic risk factors and local hemodynamics. The ensuing endothelial activation promotes the accumulation of inflammatory cells in the vessel wall. As atheroma progresses, inflammatory cells produce cytokines and growth factors, which evoke smooth muscle cell migration into the intima. The architecture of the intima changes profoundly leading to the formation of two compartment lesions, the fibrous cap and the necrotic core. Inflammatory cells may also produce matrix degrading enzymes that disrupt the integrity of the fibrous cap or procoagulant molecules such as tissue factor, ultimately leading to plaque rupture and thrombosis (Cole et al. 2011. Toll-like receptors in atherosclerosis: a "Pandora's box" of advances and controversies. Trends in Pharmacological Sciences 34:629-636).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of gastritis. A cause of gastritis is *Helicobacter pylori* colonizing the gastric mucosa causing chronic inflammation, which is characterized by enhanced expression of many inflammatory genes.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of chronic pancreatitis (CP). Chronic pancreatitis (CP) is a fibro-inflammatory disease involving the pancreatic parenchyma which is progressively destroyed and replaced by fibrotic tissues. Histologically, acinar cell damage, mononuclear cell infiltration, and fibrosis are observed. There are various causes that may lead to CP, but the exact pathophysiology of the disease is still unclear.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of psoriasis. Psoriasis is a chronic inflammatory skin disease, most commonly resulting in the occurrence of red and silver scaly plaques; it affects approximately 2-3% of the general population. Although its pathogenesis is not fully understood, there is an underlying interaction between numerous immune effector cells and aberrant hyperproliferation and differentiation of epidermal keratinocytes. It is a prototype of immune dysregulation mediated by TH1 proinflammatory cytokines such as TNF-alpha, IFN-gamma, IL-6, and IL-12 (Goldminz et al. 2012. NF-kappB: An essential transcription factor in psoriasis. Journal of Dermatological Science 69:89-94).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of congestive heart failure (CHF). CHF is a leading cause for both hospitalization and death in the western world. Its prevalence is rather increasing with the broad implementation of standardized evidence-based treatment algorithms for heart failure. The heart failure syndrome is characterized by impaired systolic and/or diastolic function and various clinical signs such as fatigue, dyspnea, fluid retention, and cachexia. An inflammatory activation in CHF patients has long been recognized. Indeed, immune mechanisms modulate interstitial fibrosis, cardiomyocyte apoptosis, and hypertrophy, all of which are central processes leading to maladaptive remodeling in response to a variety of stimuli. Especially for heart failure evolving from large myocardial infarction there is substantial evidence for a causal contribution of immunity early in the course of the disease. Systemic cytokines came have been monitored in several clinical trials. The broadest amount of data was gathered for tumor necrosis factor-alpha (TNF-alpha) which was demonstrated to correlate well with diverse clinical and laboratory parameters, such as exercise capacity and neurohormonal activation in CHF patients.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of neurodegenerative disease. In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of Alzheimer's disease (AD). AD is the most common form of dementia in the elderly resulting in a progressive decline in a number of cognitive functions including short-term memory. AD is characterized by the formation of two characteristic lesions: extracellular beta-amyloid deposits forming senile plaques and intracellular neurofibrillary tangles made up of the microtubule associated protein tau. A strong link between inflammation, primarily mediated by pro-inflammatory cytokines, and AD has been established both in clinical data and bench research. Recent findings also suggest that AD may be associated with a more widespread inflammatory state characterized by increased peripheral blood levels of IL-1, IL-6, TNF-alpha, TGF-beta, and IL-18 (Smith et al. 2012. Role of pro-inflammatory cytokines released from microglia in neurodegenerative diseases. Brain Res Bull 87:10-20).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of Parkinson's disease (PD). PD is the most common neurodegenerative movement disorder and is caused by the progressive loss of dopaminergic neurons from the substantia nigra pars compacta that normally innervate the striatum. The pathological hallmark of PD is intracellular accumulation of alpha-synuclein leading to the formation of Lewy bodies. PD may result in a number of different presenting symptoms including resting tremor, bradykinesia, cogwheel rigidity, and postural instability. Epidemiologic findings from a number of studies suggest that inflammation may be involved in the pathogenesis of PD. This is also supported, in part, by post-mortem analysis of cerebrospinal fluid and brain demonstrating elevated protein levels of pro-inflammatory cytokines in PD patients (Smith et al. 2012. Role of pro-inflammatory cytokines released from microglia in neurodegenerative diseases. Brain Res Bull 87:10-20).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of Amyotrophic Lateral Sclerosis (ALS), or Lou Gehrig's disease. ALS is a progressive fatal neurodegenerative disease that affects motor neurons in the brainstem, spinal cord, and motor cortex. ALS is universally fatal, with a median age of onset of 55 years and a survival of 2-5 years after the onset of symptoms. Prominent neuroinflammation can be easily observed in pathologically affected areas of the CNS and in spinal cords from both human ALS patients and mouse models of the disease. Typically, inflammation in ALS is characterized by gliosis and the accumulation of large numbers of activated microglia and astrocytes. Activation of glia in ALS has been extensively characterized and is marked by elevated production of potentially cytotoxic molecules such as ROS, inflammatory mediators such as COX-2, and proinflammatory cytokines such as IL-1beta, TNF-alpha, and IL-6 (Smith et al. 2012. Role of pro-inflammatory cytokines released from microglia in neurodegenerative diseases. Brain Res Bull 87:10-20).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of Huntington disease. Huntington's disease (HD) is characterized by a progressive course of disease until death 15-20 years after the first symptoms occur and is caused by a mutation with expanded CAG repeats in the huntingtin (htt) protein. Mutant htt (mhtt) in the striatum is assumed to be the main reason for neurodegeneration. Both innate and adaptive immune systems may play an important role in HD. Activation of microglia with expression of proinflammatory cytokines, impaired migration of macrophages, and deposition of complement factors in the striatum indicate an activation of the innate immune system (Ellrichmann et al. 2013. The Role of the Immune System in Huntington's Disease. Clinical and Developmental Immunology 2013: 11). Enhancement of the NFkB-mediated inflammatory response in astrocytes contributes to HD pathogenesis (Hsiao et al. 2013. A critical role of astrocyte-mediated nuclear factor-kB-dependent inflammation in Huntington's disease. Human Molecular Genetics 22:1826-1842).

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of depression or schizophrenia. Depression is associated with both a chronic low-grade inflammatory response, activation of cell-mediated immunity and activation of the compensatory anti-inflammatory reflex system (CIRS), characterized by negative immunoregulatory processes. Meta-analyses of over 100 studies provided in vivo evidence that schizophrenia can be, in part, explained by an inflammatory imbalance.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of asbestosis. Asbestosis is a chronic inflammatory and fibrotic medical condition affecting the parenchymal tissue of the lungs caused by the inhalation and retention of asbestos fibers. It usually occurs after high intensity and/or long-term exposure to asbestos (particularly in those individuals working on the production or end-use of products containing asbestos) and is therefore regarded as an occupational lung disease. Sufferers may experience severe dyspnea (shortness of breath) and are at an increased risk for certain malignancies, including lung cancer but especially mesothelioma. Asbestosis specifically refers to interstitial (parenchymal) fibrosis from asbestos, and not pleural fibrosis or plaquing. The primary symptom of asbestosis is generally the slow onset of dyspnea, especially on exertion. Clinically advanced cases of asbestosis may lead to respiratory failure. The characteristic pulmonary function finding in asbestosis is a restrictive ventilatory defect. In the more severe cases, the drastic reduction in lung function due to the stiffening of the lungs and reduced TLC may induce right-sided heart failure (cor pulmonale). In addition to a restrictive defect, asbestosis may produce reduction in diffusion capacity and arterial hypoxemia.

In an embodiment, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of silicosis. Silicosis, (previously miner's phthisis, grinder's asthma, potter's rot and other occupation-related names) is a form of occupational lung disease caused by inhalation of crystalline silica dust, and is marked by inflammation and scarring in the form of nodular lesions in the upper lobes of the lungs. It is a type of pneumoconiosis. Silicosis (particularly the acute form) is characterized by shortness of breath, cough, fever, and cyanosis (bluish skin). Signs and symptoms include: dyspnea, cough, fatigue, tachypnea, loss of appetite and weight loss, chest pain, and fever. In advanced cases, symptoms may include cyanosis, cor pulmonale, and respiratory insufficiency. Subjects with silicosis are particularly susceptible to tuberculosis (TB) infection—known as silicotuberculosis. Pulmonary complications of silicosis also include Chronic Bronchitis and airflow limitation (indistinguishable from that caused by smoking), non-tuberculous Mycobacterium infection, fungal lung infection, compensatory emphysema, and pneumothorax. There are some data revealing an association between silicosis and certain autoimmune diseases, including nephritis, Scleroderma, and Systemic Lupus Erythematosus, especially in acute or accelerated silicosis.

Methods of the invention further include administering one or more anti-inflammatory therapies to a subject. Anti-inflammatory chemotherapeutic agents are any chemical entity or drug that reduces inflammation. Anti-inflammatory chemotherapeutic agents include, but are not limited to, a nonsteroidal anti-inflammatory drug (NSAID), a glucocorticoid, methotrexate, cyclosporine, and rapamycin. NSAIDs are cyclooxygenase inhibitors. Examples of NSAIDs include aspirin, ibuprofen, naproxen sodium, diclofenac, etodolac, fenoprofen, flurbiprofen, oxaprozin. Glucocorticoids are a class of steroid hormones that bind to the glucocorticoid receptor. Methotrexate is a chemical analog of folic acid which inhibits the metabolism of folic acid. Cyclosporine and rapamycin, anti-rejection drugs, have anti-inflammatory properties.

Anti-inflammatory biologic agents are any naturally-occurring biologic entity that reduces inflammation. Anti-inflammatory biologic agents include, but are not limited to, an anti-TNF antibody, an anti-IL1 antibody, an anti-IL6 antibody, an anti-IL6 receptor antibody, an anti-IL12/23 antibody, an anti-IL17 antibody, an anti-IL1R antibody, an anti-IL1 receptor antagonist, and a soluble IL-1 receptor.

Compounds and compositions described herein can be administered as a pharmaceutical or medicament formulated with a pharmaceutically acceptable carrier. Accordingly, the compounds and compositions may be used in the manufacture of a medicament or pharmaceutical composition. Pharmaceutical compositions of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compounds may be combined with excipients such as cocoa butter, glycerin, gelatin or polyethylene glycols and molded into a suppository.

Compounds or compositions may be formulated to include other medically useful drugs or biological agents. The compounds or compositions also may be administered in conjunction with the administration of other drugs or biological agents useful for the disease or condition to which the invention compounds or compositions are directed.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound or composition, the route of administration, the rate of clearance of the compound or composition, the duration of treatment, the drugs used in combination or coincident with the compound or composition, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable. A compound can be administered parenterally, such as intravascularly, intravenously, intraarterially, intramuscularly, subcutaneously, or the like. Administration can also be orally, nasally, rectally, transdermally, intravaginally or inhalationally via an aerosol. A compound or composition can be administered to the inflammation-related lesions. The compound or composition may be administered as a bolus, or slowly infused, or be administered as an intradermal, subcutaneous or intramuscular or intraperitoneal injection.

A therapeutically effective dose can be estimated initially from cell culture assays by determining p62 expression levels upon introduction of the DNA or RNA encoding p62 into the cells. A dose can then be confirmed in animal models to achieve suppression of generation of inflammatory cytokines and/or alleviation of inflammation. Such information can be used to more accurately determine useful initial doses in humans. The exact formulation, route of administration and dosage can be chosen by medical professional in view of the subject's presentation.

EXAMPLES

Example 1

Materials and Methods
Vector Construction

As a source of cDNA encoding p62, total RNA was extracted from HeLa cells. Full length cDNA encoding the longer isoform of p62 (Transcript Variant 1, GenBank reference No. NP 003891) was amplified by PCR (HotStar HiFidelity Polymerase Kit Qiagen) using the following primers: FW: 5-CCCGCTAGCATGGCGTCGCT-CACCGTG-3 and REV: 5'-CCCAAGCTTT-CACAACGGCGGGGGATGCTTTG-3'. PCR products were purified and Nhe I-Hind III digested fragments cloned into a DNA vector with nucleic acid sequence corresponding to pcDNA3.1 resulting in p62 plasmid. A full length ovalbumin gene (pOVA) cloned in pcDNA3.1 was taken as reference plasmid. Large scale preparations of the endotoxin-free plasmids were routinely performed by alkaline lysis using either Endo Free Plasmid Kit (Qiagen) or Gen Elute HPSelect Plasmid Giga Prep columns (SIGMA #NA0800). The DNA constructs were confirmed by sequencing.

Animals and Treatments

Three-month old female FVB and Balb/c mice (Harlan Italy SrL, Correzzana Milano, Italy) were used. Mice were kept in laminar-flow cage in a standardized environmental condition. In prevention trials mice were randomly distributed in three groups (G1-G3) and injected intramuscularly at week 0, 1, 2 with only saline (G1, n=12), with pcDNA3.1 (G2, n=12), or with hp62 DNA (G3 n=12). At day forty-five after the last injection, mice from each group were randomly divided in two subgroups and were sham operated (SO; n=6) or ovariectomized (OVX n=6). After two months mice were sacrificed by CO2 narcosis according to the recommendation of the Italian Ethical Committee. For therapeutic trials mice were ovariectomized (OVX) and left untreated for 2 months. Afterwards, mice were randomized in 4 subgroups, and injected with plasmid as described above. After 2 months mice were sacrificed for analysis.

Histological Bone Analysis and Immuflourescence

Femurs, dissected of adhering tissue, were fixed in 4% paraformaldehyde (PFA) for 24 h, decalcified in 14% EDTA solution for 3 days and soaked in 30% sucrose overnight. Samples, embedded with Tissue-Tek OCT compound, were sectioned (8 µm thick sections) by a rotatory −30° C. microtome cryostat (Ames Cryostat Miles) and stained with toluidine blue. Other sections, after permeabilization with 0.3% Triton X-100 were incubated with rabbit anti-p62 diluted 1: 800 (Enzo Life Sciences; Vinci-Biochem s.r.l., Firenze, Italy) diluted 1:400. After rinsing, sections were incubated with chicken anti-rabbit IgG Alexa Fluor 488 conjugated (Molecular Probes; Invitrogen, Milano Italy) diluted 1:100. Control experiments were performed by omitting the appropriate primary antibody or by complexing the primary antibodies with the relative blocking peptide. Slides were imaged using a Leica DM 2500 fluorescent microscopy. Fluorescence analysis was performed by a fluorimeter Tecan Infinite [29].

Ex Vivo Dual-Energy X-Ray Absorptiometry (DXA) Analyses

Femurs were dissected and fixed as above described. Bone mineral density (BMD) and bone mineral content (BMC) were measured using a PIXImus DEXA.

Bone Marrow Cell (BMSC) Preparation

Long bones (femurs, tibiae and humeri) from the mouse groups were dissected free of adhering tissue. The ends were removed and the marrow cavity was flushed and cultured in DMEM.

Cytokines and Chemokines Assay

The cytokine/chemokine profiles of BMSCs supernatants were assessed by ELISA-based cytokine array by using Mouse Cytokine Array Panel A kit (R&D Systems, Milano, Italy) accordingly to the manufacturer's instructions. Immunoreactive dots were visualized using LiteAblot Turbo luminol reagents (Euroclone, Milano, Italy) and Hyperfilm-ECL film (Euroclone, Milano, Italy) and quantitated densitometrically.

Western Immunoblotting

Proteins from total bone marrow cells population were extracted in Cell Lysis Buffer (Cell Signaling Euroclone, Milano, Italy) immediately after flushing the bone marrow cavity, and the concentration was determined by the BCA protein assay reagent (Pierce, Euroclone Milano, Italy). Western blotting was performed by standard methods.

Statistical Analysis

All in vitro and in vivo experiments were repeated at least three times. t-student was used to test for significant differences between two groups, and differences were considered significant at *p<0.05.

Example 2 p62 Vaccine Prevents Osteoporosis in a Mouse Model

To evaluate whether p62 vaccine was able to prevent osteoporosis, groups of mice were first injected either with p62DNA or reference plasmids (pcDNA 3.1, pOVA) and then ovariectomized (OVX). For each trial a control group of sham operated (SO) mice was included. Two months after surgery mice were sacrificed, and the collected long bones subjected to histological examination. The metaphyseal regions of the distal femurs from pcDNA3.1-OVX (control) mice displayed classic osteoporotic features characterized by significant bone loss and thinned disconnected trabecular structure. On the other hand, p62-OVX bones (treated mice) showed a micro-architecture essentially indistinguishable to that seen in SO mice. Moreover, examination of cross sections femur diaphysis from p62DNA-OVX mice revealed (at variance of those obtained from reference plasmids treated mice) an enhanced anabolic—osteoblastic activity as evidenced by new cortical bone apposition suggesting an anabolic action of p62 treatment.

Figure 5:
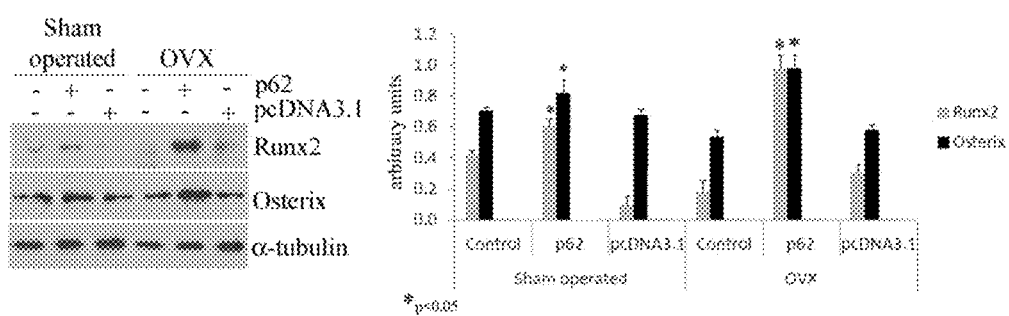
FIG. 5 shows the effect of p62/SQSTM1 DNA introduction on osteogenic markers.

BMCs were flushed from the bone cavities, and cultured for 3 days. Afterwards, both supernatants and cells were collected and analyzed respectively either for the release of inflammatory cytokines, or for expression of osteogenic markers. As shown in FIG. 4 the marked up-regulation and release of pro-inflammatory cytokines by BMCs from OVX compare to SO operated mice was drastically suppressed by p62-DNA pre-treatment. The inhibitory effect of p62 DNA extended to an array of cytokines such as TNFα, IL-6, IL-1b IL-17, all known to be essential inducers of inflammatory diseases and bone loss. As far as the capability of p62DNA to induce new bone formation is concerned, western blotting analysis of p62-OVX BMCs extracts indicated a strong and selective increase of osteogenic markers, such as Runx2 and Osterix transcription factors. An increase of Runx2 and Osterix, although weaker, was also found in p62 SO mice (FIG. 5).

Consequently, administration of p62 plasmid prevented osteoporosis in a mouse model.

Example 3 p62 Vaccine Reverses Osteoporosis in a Mouse Model

Figure 6:
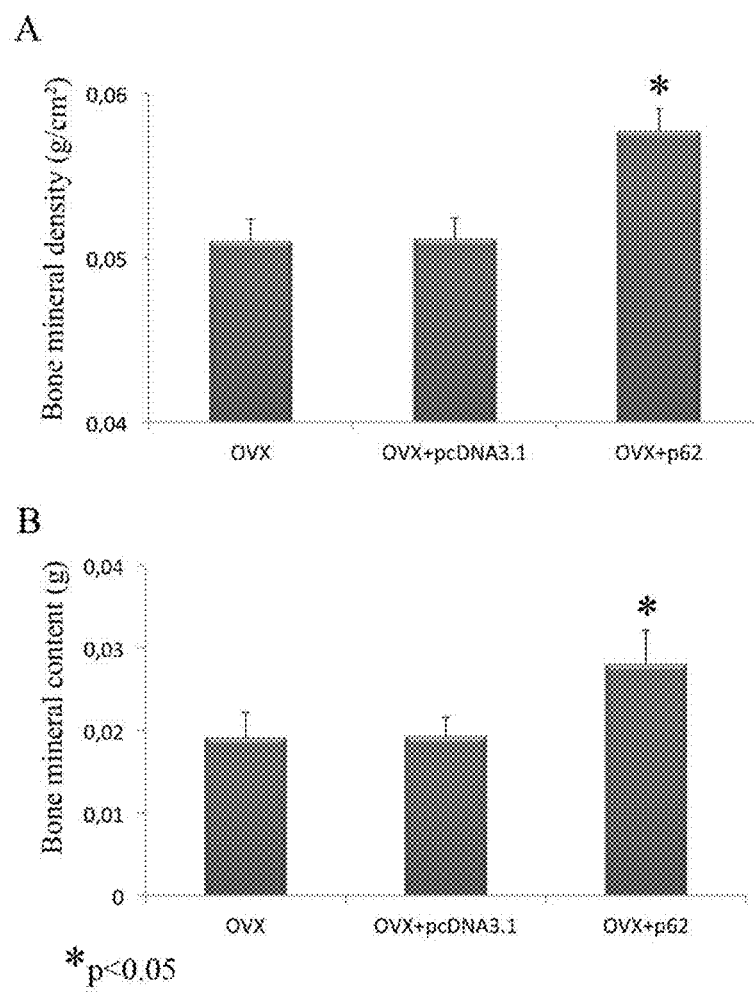
FIG. 6 shows the effect of p62/SQSTM1 DNA introduction on bone mineral density (BMD) and content (BMC)

In these trials, mice were ovariectomized and, after two months, injected either with p62-DNA or reference plasmids (see M&M for details). Two months after last plasmids injections, bones were collected and histologically evaluated. OVX-p62 treated mice group (in contrast to control groups) showed a restored trabecular microarchitecture at metaphyseal regions of the distal femurs and a decreased porosity in cortical bone. In addition, p62-DNA treatment proved to increase both bone mineral density (BMD) and content (BMC) as judged by DXA analysis (FIG. 6). Finally, coupled with marked up-regulation of osteoblastogenic Runx2 and Osterix (FIG. 7, panel A), a strong inhibition of two majors bone resorptive factors such as TNFα and RANKL was also observed in BMCs from OVX-p62 mice.

Figure 7:
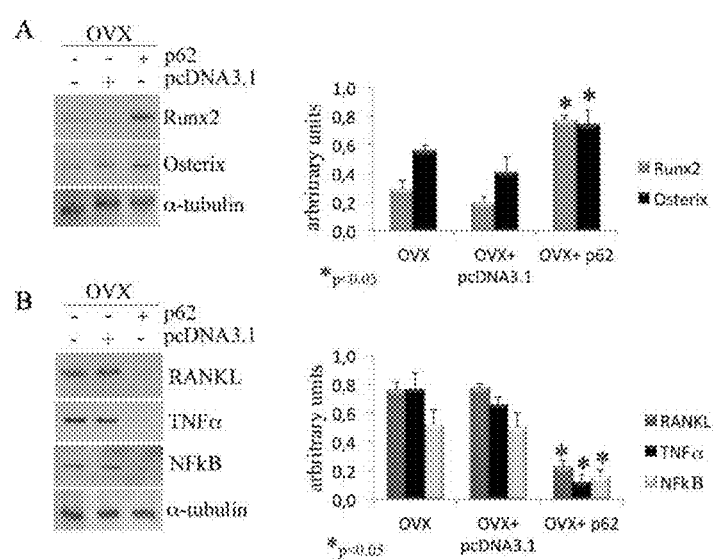
FIG. 7: Panel A shows the effect of p62/SQSTM1 DNA introduction on expression of osteogenic factors; Panel B shows the effect of p62/SQSTM1 DNA introduction on bone resorptive factors and NF-kappa-B expression.

RANKL is a key mediator of inflammation that, by binding to its receptor RANK on osteoclast precursors, fosters osteoclastogenesis via intracellular NF-kB signaling. Down-regulation of NF-kappa-B in OVX-p62 BMCs was also observed (FIG. 7, panel B). Consequently, p62 administration reversed osteoporosis in a mouse model.

Example 4 p62 Vaccine Upregulates Endogenous p62 in a Mouse Model

Figure 8:
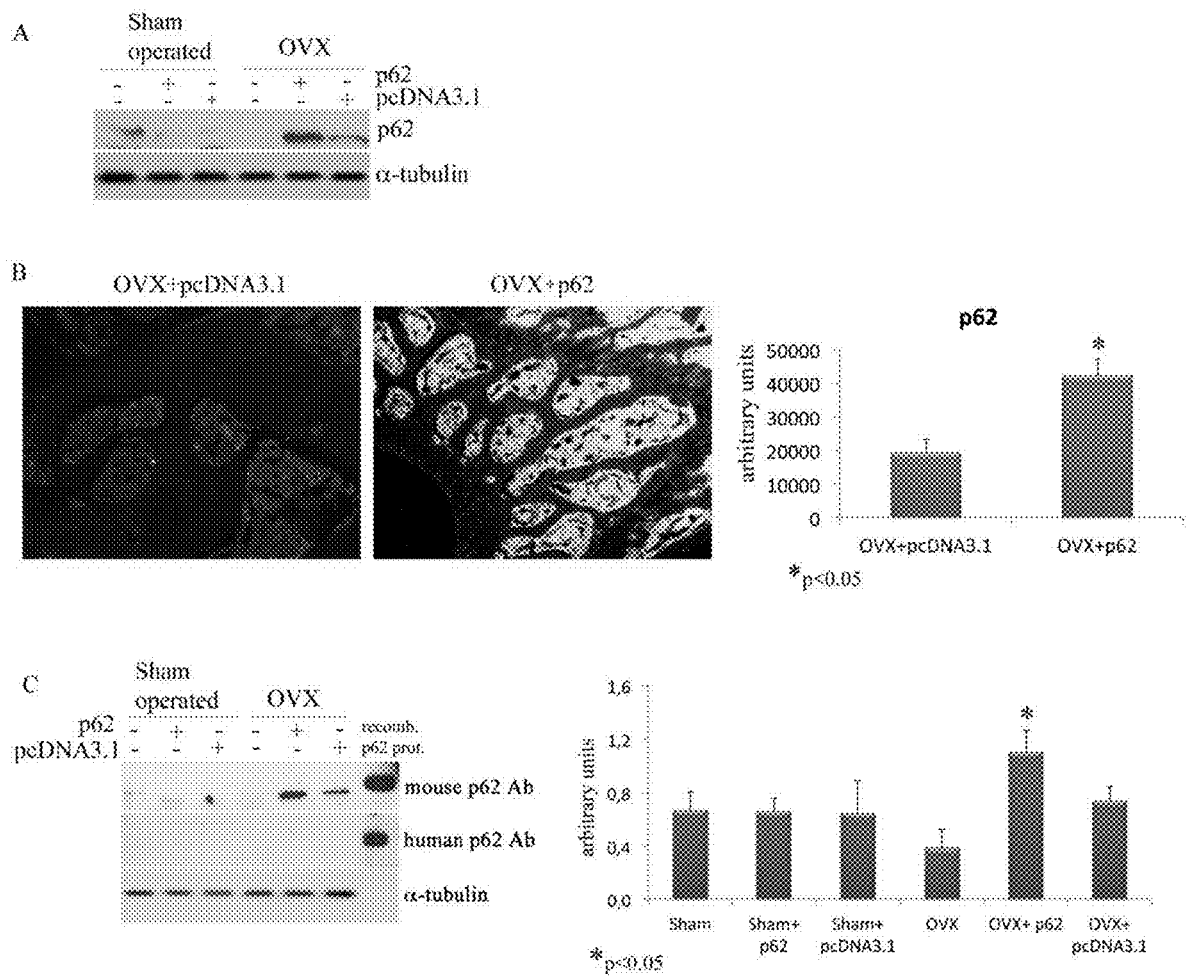
FIG. 8: Panel A shows the effect of exogenous p62 on p62 expression; Panel B shows increase p62-immune labelling at the epiphyseal region of femurs of p62-OVX mice; Panel C Western Blots demonstrate that the increased level of p62 is from endogenous p62.

The expression levels of p62 in BMCs retrieved from plasmids injected mice before ovariectomy were determined. Surprisingly, although p62 expression in BMCs was down-regulated by ovariectomy, BMCs from p62 DNA pre-injected mice demonstrated up-regulation of p62 (FIG. 8, panel A). Consistently, an increased p62-immune labeling was observed at the epiphyseal region of femurs of p62-OVX mice (FIG. 8, panel B).

Western Blotting analysis that can distinguish between human (exogenous) and mouse (endogenous) p62 was performed. As shown in FIG. 8, panel C, p62DNA administration up-regulates endogenous p62 protein in bone marrow-resident cells. Consequently, administration of p62 plasmid increased endogenous p62 levels in a mouse model.

Figure 9:
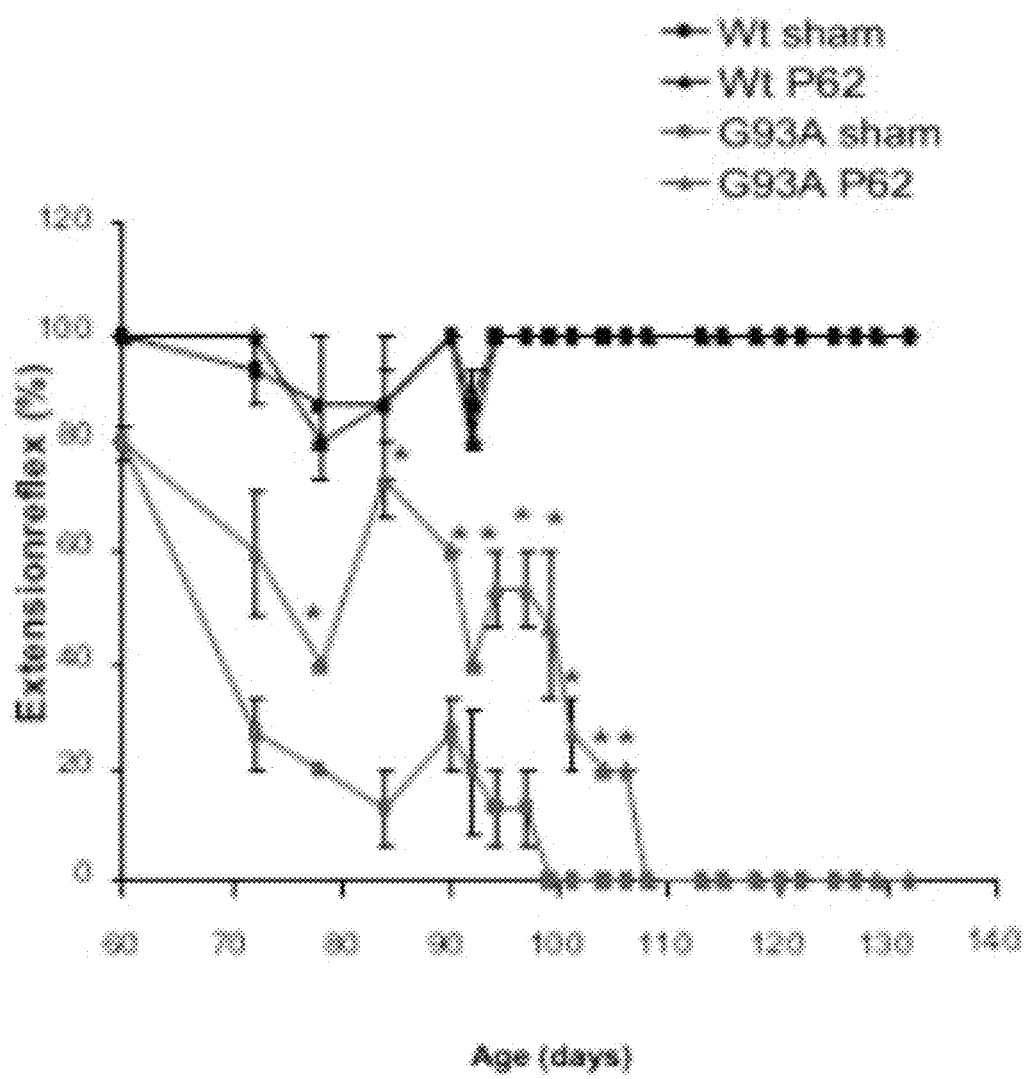
FIG. 9 shows the effect of p62/SQSTM1 DNA introduction on a mouse model of ALS.

Example 5 p62 Administration Reduced Symptoms of Amyotrophic Lateral Sclerosis (ALS) in a Mouse Model FIG. 9 shows the effect of p62 on a mouse model of ALS. Neuroinflammation is a prominent pathologic feature in the spinal cord of patients with ALS, and is characterized by glial activation and infiltrating T cells. A similar inflammatory response is present in spinal cords of ALS mice. This is the most common mouse model of ALS expressing G93A mutant form of SOD, the same mutation which occurs in a humans with ALS, and this model is widely used for testing of drugs against ALS. Mice were treated with p62 plasmid or pcDNA 3.1 plasmids (6 times weekly with 150 ug/mouse i.m.) from day 75 after birth (6 mice per group), and a standard test for ALS (hind limb extension reflex) was applied. This reflex was evaluated as the ability to perform complete extension of the hind limbs when the animal was suspended by the tail. Without ALS, both control and p62 treated mice demonstrate strong reflex, which started to decline in ALS mice after 60 days of age, and it decreased from 100% to zero on 100 days. Treatment with p62, however, markedly delayed decline in the reflex. Consequently, administration of p62 plasmid reduced symptoms related to ALS in a mouse model.

Example 6 p62 Administration Reduced Symptoms of Multiple Sclerosis (MS) in a Mouse Model

Figure 10:
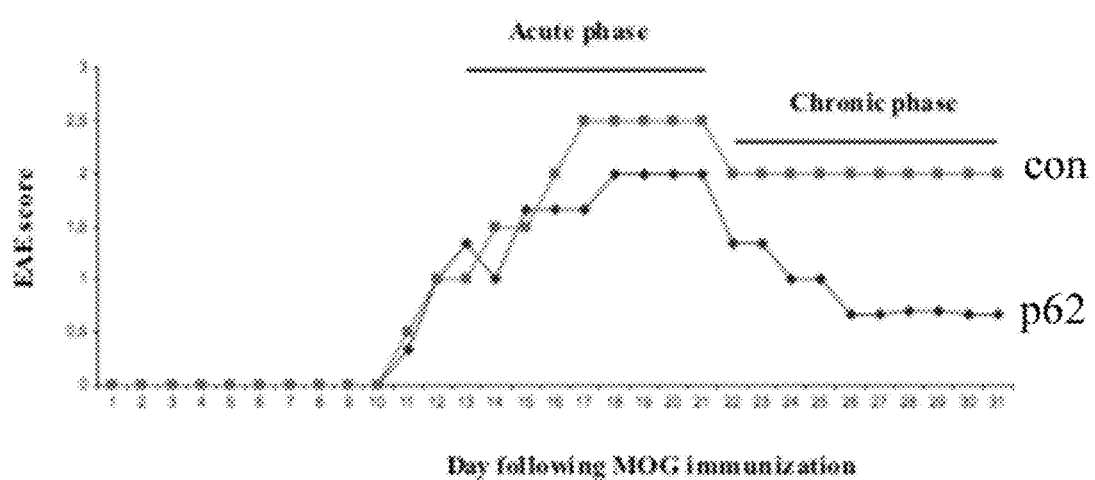
FIG. 10 shows the effect of p62/SQSTM1 DNA introduction on a mouse model of MS.
Figure 11:
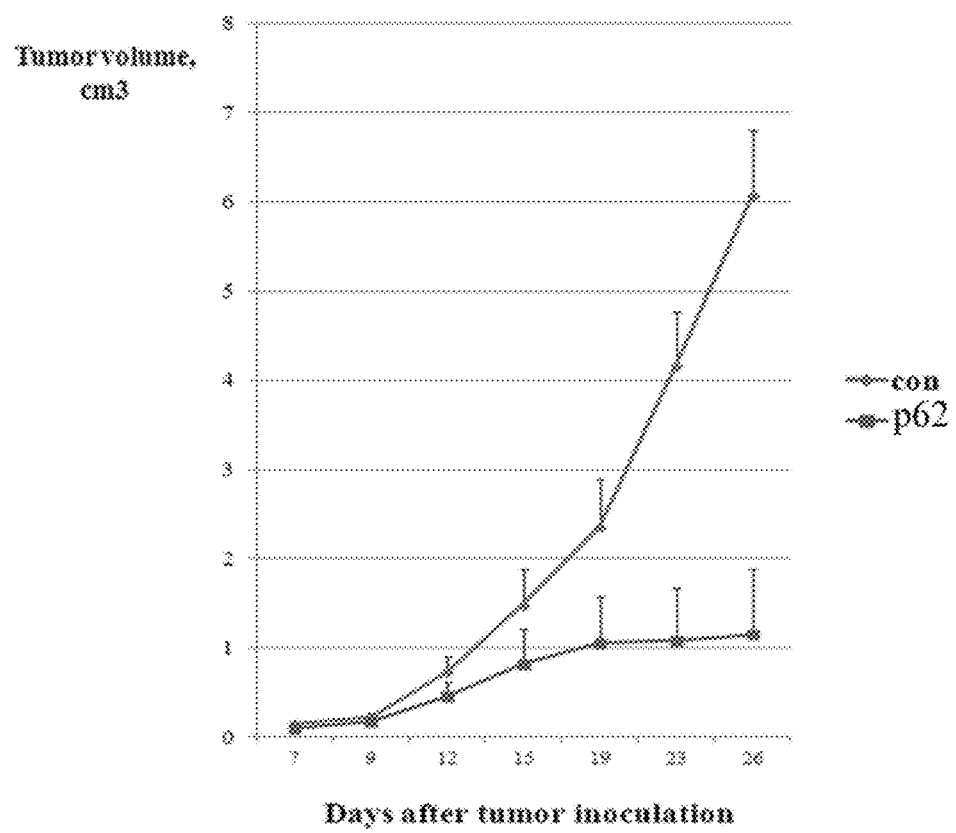
FIG. 11 shows the effect of p62/SQSTM1 DNA introduction on growth of S37 sarcoma.

MS is a chronic inflammatory disease resulting in demyelination and axonal loss throughout the central nervous system (CNS), with unknown cause and only limited treatment options (Noseworthy, J. H., C. Lucchinetti, et al. (2000)"Multiple sclerosis." N Engl J Med 343(13): 938-52.; Lassmann et al., 2001 "Heterogeneity of multiple sclerosis pathogenesis: implications for diagnosis and therapy." Trends Mol Med 7(3): 115-21). The most commonly used animal model for MS research is murine experimental allergic encephalomyelitis (EAE) induced by administration of MOG polypeptides. This model resembles both the inflammatory phase, i.e., the generation of autoreactive myelin specific T cells, as well as the neurodegenerative phase of the disease, i.e., destruction of the myelin sheath around the axons and subsequent loss of axons, as observed in human disease (Steinman, 2001, "Multiple sclerosis: a two-stage disease." Nat Immunol 2(9): 762-4.). FIG. 10 demonstrates clinical signs of rMOG-induced EAE showing mean clinical scores. Mice (4 per group) were examined daily for clinical signs of EAE and were scored as followed: 0, no disease; 1, limp tail; 2, hind limb weakness; 3, complete hind limb paralysis; 4, hind limb paralysis plus forelimb paralysis; and 5, moribund or dead. On day 0 MOG immunization. p62 DNA (100 µg/50p1) administered at days 16 and 22 after MOG immunization as indicated by red arrows. As one can see, whereas control mice had higher EAE score till the end of observation (day 31), in mice treated with p62 plasmid this score progressively declined (to about 0.5 at day 31). Consequently, administration of p62 plasmid alleviated MS-like symptoms in a mouse model of MS.

Example 7 p62 Administration on Tumor Growth and Mouse Survival

Figure 12:
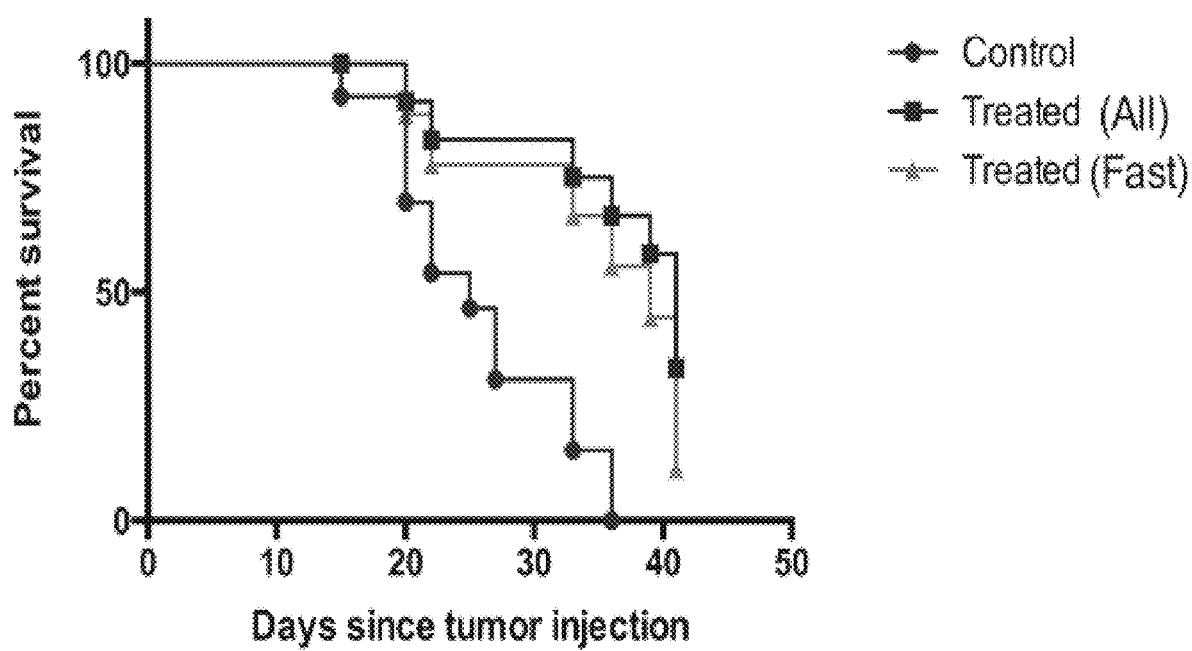
FIG. 12 shows the effect of p62/SQSTM1 DNA introduction on survival of mice with breast carcinoma.

Chronic inflammation is involved in pathogenesis of sarcomas, in particular, Kaposi sarcoma (Douglas J L, 2010 "Kaposi Sarcoma Pathogenesis: A Triad of Viral Infection, Oncogenesis and Chronic Inflammation." Transl Biomed 1(2). Transplantable sarcoma 37 in mice was used to study effect of p62 vaccination on tumor growth. Mice (6 per group) were injected i.m. with p62 plasmid or empty vector (250 ug per mouse) 14, 7 days before 1, 8, 14 days after tumor inoculation and growth of tumors was monitored by caliper. Injection of p62 plasmid almost completely prevented growth of sarcoma 37. Consequently, administration of p62 plasmid reduced growth of mouse S37 sarcoma Chronic inflammation accompanies breast cancer, and increased levels of IL-6 is a negative prognostic factor Lippitz, B. E. (2013). "Cytokine patterns in patients with cancer: a systematic review." The Lancet Oncology 14(6): e218-e228. There is specific form of breast cancer, IBC (inflammatory breast cancer) which is the most aggressive and with poor prognosis (Fernandez, Robertson et al. 2013 "Inflammatory breast cancer (IBC): clues for targeted therapies." Breast Cancer Research and Treatment 140(1): 23-33). To study effect of p62 vaccination on survival of mice with Ca755 breast cancer, mice were treated with p62 polynucleotide and their survival was monitored. Treatment with p62 increased mouse mean survival with breast cancer by 56% (from 25 to 39 days) both in fast and slow-growing tumors (FIG. 12).

Example 8

Effect of p62 Polynucleotide Administration on Tumor Metastases

Figure 13:
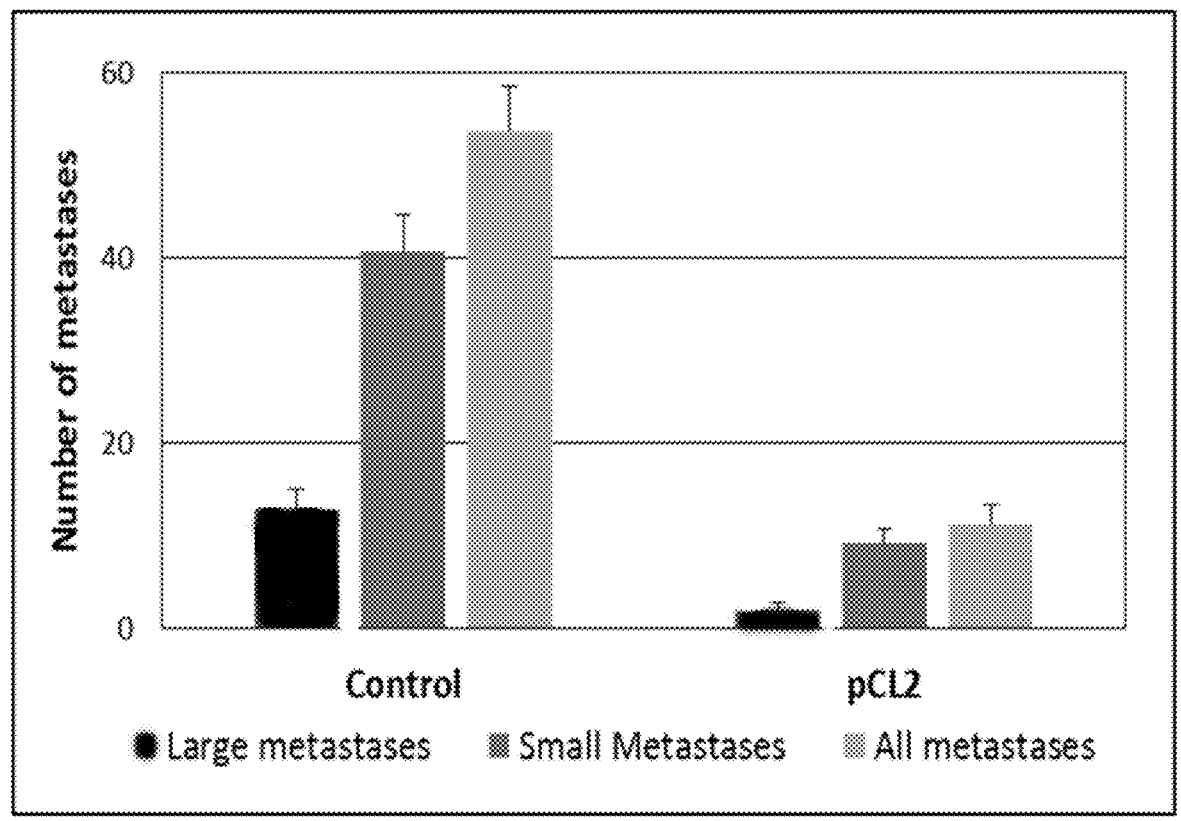
FIG. 13 shows the effect of p62/SQSTM1 DNA introduction on metastasis in LLC; and, FIG. 14 shows the effect of p62/SQSTM1 DNA introduction on metastasis in B16 melanoma.

LLC is a widely used model of metastatic lung cancer: after subcutaneous inoculation of tumor cells in flanks of mice, within 3 weeks they form metastases in lungs which can be easily counted. Treatment of mice with p62 polynucleotide markedly suppresses formation of both small and big metastases thus effectively blocking metastatic process (FIG. 13). Consequently, administration of p62 plasmid suppresses lung cancer in a mouse model.

Figure 14:
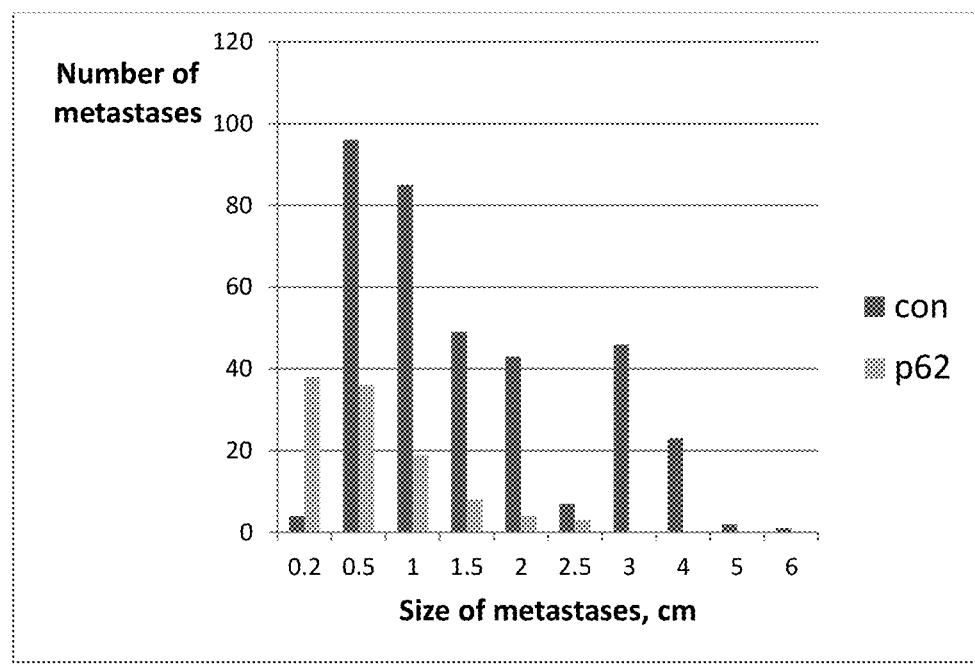

B16 melanoma cells were injected intravenously (in tail vein), thereby imitating a clinical situation wherein cancer is diagnosed when tumor cells are already in blood stream. Tumor cells forms metastases in the lung, which can be detected and counted. p62 polynucleotide was administered 1, 8, 15 days after tumor cell inoculation. As seen in FIG. 14, treatment with p62 polynucleotide significantly reduced number and size of metastatic tumors, thereby demonstrating ant-metastatic effect.

Example 9

Obesity and Metabolic Syndrome

Three groups of newborn male mice received subcutaneous injections of i) placebo or ii) and iii) 3 mg/kg of monosodium glutamate (MSG) daily for 10 days. Group 3 then received 5 weekly injections of 200 ug of p62-encoding plasmid intramuscularly. Body weight of animas in all 3 groups was measured and compared. MSG markedly increased body weight in both groups compared to the control group (p<0.01 and p<0.05). However, increase of body weight in the group receiving p62 plasmid was significantly less than in a group receiving MSG alone. Consequently, administration of the p62-encoding plasmid reduced obesity in the mouse model.

Example 10

Type 2 Diabetes

Two groups of Zucker Diabetic Fatty (ZDF) rats, a standard model for Type 2 Diabetes, were fed with 6.5% fatty diet. One group received 5 weekly injections of p62 plasmid, 200 ug/injection, while another was used as a control. In the control group hyperglycemia was observed between 8 and 10 weeks of age, while in the plasmid treated group hyperglycemia was delayed an average of 3 weeks. Consequently, administration of the p62 plasmid delayed the incidence of Type 2 Diabetes in the rat model.

Example 11

Fat Liver

Two groups of mice were fed with MCD diet (10% fat, 40% sucrose, no choline, no methionine). Each group contained 15 mice. Serum level of alanine aminotransferase (ALT) was monitored starting at 10 weeks on the diet. An experimental group received 5 weekly intramuscular injections of p62-encoding plasmid, 200 ug/injection. The placebo group received MCD diet with no plasmid intervention. Control group received normal diet and no plasmid through the entire research period. Both groups dieting on MCD have demonstrated elevated level of ALT compared to the control group (p<0.01 for both groups). However, p62 treatment reduced ALT level compared to placebo group (p<0.05). Consequently, administration of the p62 plasmid reduced the incidence of fat liver disease in the mouse model.

Example 12

Crohn's Disease

Mice received drinking water containing 8% dextran sulfate sodium (DSS) for 2 weeks. Contemporarily, one group of mice received 5 weekly in injections of 200 ug of p62-encoding plasmid while the other group constituted the control (10 animals in each group). p62-treated animals demonstrated reduction in bloody stool and diarrhea. Also, the weight of each animal was monitored individually once a week. p62 inhibited weight loss (p<0.05) although it did not entirely stop it. Consequently, administration of the p62 plasmid reduced symptoms related to Crohn's Disease in a mouse model.

Example 13

Pancreatitis

Mice were treated with 4 mg/animal LPS and 1 ug per animal caerulein for 10 weeks, twice a week, to induce pancreatitis. 3 mice were used as a control group, and 3 received 5 weekly injections of p62 vaccine 200 ug/injection intramuscularly. After 15 weeks mice were sacrificed and subjected to histological analysis. p62 plasmid treatment reduced the extent of observed chronic pancreatitis. Consequently, administration of the p62 plasmid reduced pancreatitis in a mouse model.

Example 14

Asthma

Mice were subjected to three intraperitoneal injections of 1% ovalbumin solution. Injections were made with 14 days intervals. A week after the 3d injection animals were exposed to a 1% ovalbumin aerosol for 30 min each day for 3 days to induce asthma-like disease. During this 5 weeks period, one group of mice received 5 weekly intramuscular injections of 200 ug of p62 plasmid, while another was kept as a control. Two days after the final exposure, airway hyperresponsiveness (AHR) was measured and compared in control and treatment group. AHR was induced either by cold air or by hyperventilation. AHR manifestation was significantly reduced in p62-treated group. Consequently, administration of the p62 plasmid reduced asthma symptoms in a mouse model.

Example 15

Arthritis Osteoarthritis

Two groups of mice (10 animals per group) were administered collagen II (CII) with complete Freund adjuvant to induce collagen-induced arthritis. Animals were 6 weeks of age to avoid spontaneous arthritis, which can be observed in older animals. An experimental group also received 5 weekly injections of 200 uf of p62-encoding plasmid. The control group manifested first signs on arthritis 30-33 weeks after the CII challenge. The p62-treated group demonstrated collagen-induced arthritis 38-43 weeks after CII injections. Consequently, administration of the p62 plasmid delayed collagen-induced arthritis in a mouse model.

Example 16

Atherosclerosis

ApoE(-/-) mice were maintained on a high-fat diet for 8 wks. The control group was not vaccinated while the experimental group received 5 weekly injections of 200 ug of p62-encoding plasmid. The plasmid treatment reduced the atherosclerotic plaque area and plaque neovessel density. It increased the plaque collagen and elastin contents, and reduced plasma angiotensin II levels and plaque macrophage infiltration and cathepsin S (CatS) protein. p62 administration also decreased the levels of AT1R, gp91phox, TLR2, monocyte chemotactic protein-1 in the aortic roots. Consequently, administration of the p62 plasmid reduced atherosclerosis in a mouse model.

Example 17

Parkinson's Disease

Male Wistar rats were either pretreated with 5 weekly injections of p62-encoding plasmid, 200 ug/injections, or used as a control group. Then, 6-hydroxydopamine, 6-OHDA (10 micrograms in 0.1% ascorbic acid in normal saline) was administered to experimental and control groups rats via unilateral intrastriatal injection to simulate Parkinson's Disease. Three weeks after 6-OHDA infusion, rats were tested for neurobehavioral activity (open-field test and rotarod muscular coordination test). A control group which received neither the plasmid nor 6-OHDA was utilized to assess the effect of 6-OHDA. Pretreatment with p62 plasmid markedly reduced Parkinson's-like manifestation induced by 6-OHDA in the rat model.

Example 18

Huntington's and Alzheimer's Disease.

Ovariectomy induces neurodegenerative changes analogous to Huntington and Alzheimer's diseases in the mouse. Mice were subjected to sham operation or ovariectomy. Both operated groups were divided in 2 sub-groups: one subgroup received p62-plasmid vaccination, and another did not. A battery of behavioral tests were conducted as described below. In each test we have observed that p62 vaccination significantly alleviated the neurodegenerative effect of ovariectomy, which indicates it may have strong potential in treatment and/or prevention of Alzheimer's and Huntington's diseases.

Behavioral Tests

All experiments were performed during the light period in accordance with the European Community Council Directive for Care and Use of Laboratory Animals (86/609/EEC).

Behavioral testing took place during four consecutive days. On the first day, animals were subjected to the whole battery of sensorimotor tests. On the second day, open field was performed. On the third day, animals were subjected to the Porsolt-test. Finally, the plus-maze test or light/dark test was performed on the last day.

The sequence of testing was based on previous reports by different authors (Johansson et al., Proc Natl Acad Sci USA. 2001 Jul. 31; 98(16):9407-12 and Giménez-Llort et al., Eur J Neurosci. 2002 August; 16(3):547-50; Baeza et al., J Neuroimmunol. 2010 Feb. 26; 219(1-2):90-9). Behavior was evaluated by three independent observers. Mice were weighted before performing the tests, in order to be sure that all of them were active in the same way. Olfactory trails were removed by cleaning the surface of the apparatuses after each test.

Sensorimotor Abilities

Visual Placing Reflex

The visual placing reflex was tested in order to evaluate the function of the visual system. For the performance of this placing response, the mouse was suspended by the tail and lowered toward a solid black surface. Complete extension of the forelimbs was considered a positive response. The mean response was rated in three trials (Baeza et al., 2010).

Hindlimb Extensor Reflex

This reflex was evaluated during the previous test as the ability to perform complete extension of the hindlimbs when the animal was suspended by the tail. Such response was considered positive. The mean response was rated in three trials (Baeza et al., 2010).

Tightrope Test

This method is used to evaluate the vitality loss in aging mice by testing their muscular vigor, motor coordination and traction in two training trials of 5 s and a test trial of 60 s (Miguel and Blasco, Ex p Gerontol. 1978; 13(6):389-96 and Baeza et al., 2010). Mice were suspended by their forelimbs in the middle of an elevated horizontal tightrope (40 cm height, 60 cm length and divided in segments of 10 cm). Muscular vigor was assessed as the percentage of mice falling off the rope and the latency to fall (in seconds). Motor coordination included the percentage of mice that walk at least 1 segment (criteria 1) and the percentage of mice that complete the test (criteria 2). Traction was evaluated by analyzing the different parts of the body that mice used to remain suspended (forelimbs, hindlimbs and tail) and, subsequently, the percentages of mice displaying the maximum (forelimbs, hindlimbs and tail) and minimum (forelimbs only) traction capacities were assessed within each group.

Exploratory and Anxiety-Like Behavioral Tests

This group includes different tests that study the depressive-like and anxiety-like behaviors in the animals: the FST, the open field, the light/dark and the EPM tests.

Forced Swimming Test (FST)

The forced-swimming test is the best recognized pharmacological model for assessing antidepressant-like activity in rodents (Porsolt et al., 1977a Arch Int Pharmacodyn Ther 229: 327-336, Porsolt et al., 1977b Nature 266: 730-732; Willner, 1990 Pharmacol Ther 45: 425-455; Al-Rahbi et al., Biomed Res Int. 2013; 2013:493643. doi: 10.1155/2013/493643). The development of learned helplessness syndrome, when mice are placed in a cylinder filled with water that they cannot escape from, reflects the cessation of persistent escape-directed behavior, as seen by increased periods of immobility (Lucki, 1997 Behav Pharmacol 8: 523-532). The reduction in immobility is considered as a behavioral profile that is consistent with an antidepressant-like action (Cryan et al., 2002 Trends Pharmacol Sci 23: 238-245; Walf and Frye., 2010 Physiol Behav. 2010 Feb. 9; 99(2):169-74; Al-Rahbi et al., 2013). Briefly, the mice were placed individually in a glass cylinder (20 cm in height, 14 cm in diameter) filled to a 15 cm depth with water ($23\pm1°$ C.). At this water depth, the mice could touch the bottom of the jar with their tail, but they could not support themselves with their hind limbs. Each mouse was given a 6 min swimming test, and the duration of immobility was noted during the final 4 min interval of the test, since the first 2 min were used to allow the animals to familiarize them-selves with the surroundings. All the swim-test sessions were recorded by a video camera positioned directly above the cylinder. Two experienced observers, who were blind to the treatment conditions, scored the videotapes. An immobility period was regarded as the time spent by the mouse floating in the water without struggling and while making only the very slight movements that are necessary to keep its head above the water. Following these swimming sessions, the mice were towel dried and returned to their housing. Each animal was tested only once.

Open Field Test

Locomotor activity was measured by an open-field apparatus consisting of a square arena (43.2 cm×43.2 cm) equipped with two lines of 16 photocells to measure horizontal and vertical activity. The arena was lit by one red light lamp (25 W), and a white noise generator in the room produced an ambient background noise of ~70 dB. All data were recorded on a personal computer (MED-PC Open-Field Activity Software) in an adjacent control room. Mice were placed in the centre of the apparatus and the test was carried out for 5 min. A number of conventional and ethological parameters (Choleris et al., 2001 Neurosci Biobehav Rev 25: 353-360; Perfumi and Mattioli, Phytother Res. 2007 January; 21(1):37-43) were collected during the session. The horizontal activity (i.e. distance travelled, ambulation time, resting time) and the vertical activity (i.e. rearing) in the central and peripheral zone were recorded automatically. The time spent in the central area, the ambulation time and vertical activity in this zone, and the latency to leave the starting central point and that to reach the periphery ("freezing behavior") were measured as indicators of the emotional reactivity of the mouse (Baeza et al., 2010). Moreover aging involves a decrease in the defecatory behaviour and an increase of urine incontinence. Therefore, the number of fecal boli and presence of urine were also considered in the different groups of age (in an attempt to study whether ovariectomy in mature animals caused these behaviors to be more similar to those observed in aged animals).

Light/Dark Test

A relevant test system to detect anxiety-related behaviour in mice is the light/dark exploration test, which uses the aversion of rodents for brightly lit large spaces (Hascoet et al., 2001 Prog Neuropsychopharmacol Biol Psychiatry 25: 141-166; Bourin and Hascoet, 2003 Eur J Pharmacol 463: 55-65). The light-dark apparatus consisted of an open-topped rectangular Plexiglas box (45×30×30 cm; l×b×h) that was divided into a small (18×30 cm) area and a large (27×30 cm) area with an opening door (7.5×7.5 cm) located in the center of the partition at floor level. The small compartment was painted black and stayed dark, whereas the large compartment was painted white and was brightly illuminated with a 60 W (400 lx) light source. Briefly, each animal was placed at the center of the illuminated compartment, facing one of the dark areas. The latency time for their first passage from the light compartment to the dark one, the number of entries into each compartment, the time spent in the illuminated area, and the number of times that the mouse reared on its hindpaws in the light space (rearing), were recorded for 5 min (Waif and Frye., 2010).

Elevated Plus Maze Test (EPM)

The elevated plus maze assesses anxiety-like behavior and consisted of black Plexiglas with two open arms (30×3.5 cm) and two enclosed arms of the same size (14 cm high walls). The four arms were connected by a central square (6×6 cm square) and were elevated approximately 74 cm from the ground. Briefly, mice were placed in the central square facing one of the closed arms and its behavior was scored for 5 min. The number of entries with all four paws within the arms and the time spent in the arms were scored separately for open and closed arms. A greater amount of raw time and a greater proportion of time (%) spent on the brightly-lit open arms of the elevated plus maze was considered an index of anxiety-like behavior (Kolosova et al., Aging (Albany N.Y.). 2013 June; 5(6):474-84; Walf and Frye., 2010).

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for treating, alleviating, ameliorating, relieving, delaying onset of, inhibiting progression of, reducing severity of, and/or reducing incidence of one or more symptoms of a non-cancer-related chronic inflammatory disease in a subject in need, said method comprising administering to said subject an agent comprising p62/SQSTM1 nucleic acid that encodes a polypeptide at least 90% identical to SEQ ID NO: 2, wherein said agent suppresses the expression of a proinflammatory cytokine in a subject, and wherein said non-cancer-related chronic inflammatory disease is a neurodegenerative disease selected from the group consisting of: amyotrophic lateral sclerosis, Parkinson's disease, Huntington's disease, and Alzheimer's disease.

2. The method of claim 1, further comprising administering one or more anti-inflammatory therapies.

3. The method of claim 2, wherein said one or more anti-inflammatory therapies is selected from the group consisting of: anti-inflammatory chemotherapeutic agent and biological agent.

4. The method of claim 3, wherein said anti-inflammatory chemotherapeutic agent is selected from the group consisting of: a nonsteroidal anti-inflammatory drug, a glucocorticoid, methotrexate, cyclosporine, and rapamycin.

5. The method of claim 3, wherein said biological agent is selected from the group consisting of: an anti-TNF antibody, an anti-1L1 antibody, an anti-IL6 antibody, an anti-1 L6 receptor antibody, an anti-1L12/23 antibody, an anti-1L17 antibody, an anti-1L1 R antibody, an anti-1L1 receptor antagonist, and a soluble IL-1 receptor.

6. The method of claim 1, wherein said proinflammatory cytokine is selected from the group consisting of: TNF-alpha, IL-6, IL-1 beta, RANTES, IL-17, IL-23, CCL-1, MCP-5, and CXCL2.

* * * * *